(12) United States Patent
Tsuzuki et al.

(10) Patent No.: US 10,968,457 B2
(45) Date of Patent: Apr. 6, 2021

(54) DRUG-INDUCIBLE PROMOTER AND METHOD OF INDUCTING GENE EXPRESSION USING THE SAME

(71) Applicant: TOYOTA JIDOSHA KABUSHIKI KAISHA, Toyota (JP)

(72) Inventors: Shoko Tsuzuki, Toyota (JP); Satoru Nishimura, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 507 days.

(21) Appl. No.: 15/190,990

(22) Filed: Jun. 23, 2016

(65) Prior Publication Data

US 2017/0107528 A1  Apr. 20, 2017

(30) Foreign Application Priority Data

Jun. 25, 2015  (JP) .............................. JP2015-128038

(51) Int. Cl.
*C12N 15/63* (2006.01)
*C12N 15/82* (2006.01)

(52) U.S. Cl.
CPC ..... *C12N 15/8238* (2013.01); *C12N 15/8241* (2013.01)

(58) Field of Classification Search
None
See application file for complete search history.

(56) References Cited

U.S. PATENT DOCUMENTS

| 2012/0096600 A1 | 4/2012 | Ruiter et al. |
| 2013/0291231 A1 | 10/2013 | Hattori et al. |
| 2013/0291232 A1 | 10/2013 | Hattori et al. |
| 2015/0135373 A1 | 5/2015 | Nishimura et al. |

FOREIGN PATENT DOCUMENTS

| AR | 077305 A1 | 8/2011 |
| JP | 3527585 B2 | 5/2004 |
| JP | 4566993 B2 | 10/2010 |
| JP | 2011-188758 A | 9/2011 |
| JP | 2014-3917 A | 1/2014 |
| JP | 5472089 B2 | 4/2014 |
| JP | 5655947 B2 | 1/2015 |
| NZ | 568867 A | 12/2010 |
| WO | 2014/136793 A1 | 9/2014 |

OTHER PUBLICATIONS

Shokouhifar et al (Biologia Plantarum, 2011, 55(4):689-695).*
Romer et al (Plant Physiol., 2009, 150: 1697-1712).*
De Lange et al (Current Opinion in Biotechnology, 2018, 49: 16-22).*
Venter et al (Plant Developmental Biology —Biotechnology Perspectives: vol. 2, 2010, Chapter 20, pp. 393-414).*
Noutoshi et al (Frontiers in Plant Science, 2012, 3(245): 1-10).*
Mehrotra et al (Plant Mol. Biol., 2011, 75:527-536).*
Alan H. Christensen, et al., "Maize polyubiquitin genes: structure, thermal perturbation of expression and transcript splicing, and promoter activity following transfer to protoplasts by electroporation", Plant Molecular Biology, 1992, pp. 675-689, vol. 18, No. 4.
Gil A. Enriquez-Obregon, et al., "Herbicide-resistant sugarcane (*Saccharum officinarum* L.) plants by *Agrobacterium*-mediated transformation", Planta, 1998, pp. 20-27, vol. 206.
Christiane Gatz, "Chemically inducible promoters in transgenic plants", Current Opinion in Biotechnology, Plant biotechnology, Apr. 1, 1996, vol. 7, No. 2, pp. 168-172 (5 pages total).
Lieven De Veylder et al., "Herbicide Safener-Inducible Gene Expression in *Arabidopsis thaliana*", Plant Cell Physiology, Jan. 1, 1997, vol. 38, No. 5, pp. 568-577 (10 pages total).

* cited by examiner

*Primary Examiner* — Stephen Uyeno

(74) *Attorney, Agent, or Firm* — Sughrue Mion, PLLC

(57) ABSTRACT

This invention provides a drug-inducible promoter that can be used for sugarcane plants and plants related thereto. Such drug-inducible promoter comprises a polynucleotide comprising a first nucleotide sequence having 90% or higher identity to the nucleotide sequence as shown in SEQ ID NO: 1, a second nucleotide sequence having 90% or higher identity to the nucleotide sequence as shown in SEQ NO: 2, a third nucleotide sequence having 90% or higher identity to the nucleotide sequence as shown in SEQ ID NO: 3, a fourth nucleotide sequence having 90% or higher identity to the nucleotide sequence as shown in SEQ ID NO: 4, and a fifth nucleotide sequence having 90% or higher identity to the nucleotide sequence as shown in SEQ ID NO: 5 in such an order from the 3 terminal side toward the 5' terminal side.

9 Claims, 12 Drawing Sheets

Specification includes a Sequence Listing.

Fig. 2-1

Query Range: 196 - 2110
Sbjct Range: 1 - 1912
1985 bp, INT.Score: 140, OPT.Score: 1408
Identity: 1048 / 1985 (52%)
Similarity: 1048 / 1985 (52%)
Strand: Plus / Plus

```
Query  196   GATTAAAGTCACTAT--AATTTGACTAAGGACAAAACGGGATTACTTATATTTTAGGCCA  253
             ||| ||||||    || ||  ||   |  |   |   |   |   |   |||    |||  |
Sbjct  1     GATCAAAGTTGTTTTGCAACCTCGAACATGCTAGCCCTTGCTGGCGTGTGACTTAATTCG  60

Query  254   GAGGGAGTACCGTTTAATTTGTCTCGATTGGTCCATAATTTCTCCAACTATTATAAACTT  313
             |     |||    |   |||   ||| | ||   ||    |   |||    |||| |||
Sbjct  61    GCATCAATAGTATCAGATATGTATGTATGCCTTTAT-GTTTGTGAATCTAATGTACTGTA  119

Query  314   CT--TGT-TTCATTTTATTTATATTTGCT----GAGTGTATGTGGGA-------CGCACCTTTTGT  365
             ||  ||| |||    ||  | ||| |||      |||||| ||       ||  ||  |||
Sbjct  120   ATGTGTGTGAACTATAACGAGATTCTCTACTACAATATGTGCGAGGGGCACAAATTATGT  179

Query  366   ---TGCAG--GATATTGATGTAAGGAAT-TCCAGGCGGCGA-GTCTCTGCATCTAATTTGGT  420
                |   |  ||||  ||  ||| |  | ||||     |  | |||| ||    |   ||
Sbjct  180   CCTAATGTGGTATTATTGGGCTGATTGTATTTGTGTCCACGCCCATGCACTTGTTCATGT  239

Query  421   ACCAGTAGAAACCGGAGCATACCCTCCCATGAACTGCTATAATCCTTCATTAGAAGTAGC  480
             |  || |||| |   || |||   |  | || ||     |||   ||  ||| ||| |
Sbjct  240   A-TTGTTGAACCTGTAGCTTTTCTCCCAATGTCAGACGGTGATATTTATTTTCAAAACT  298

Query  481   GC-TGCATCTTACTCAATCCAGATT-TCCACGGCGTTCTTCGAA--GGACTGGA-TAACT  535
             || ||| |   || |  ||   || ||||   |||| |  |    |||  | | | |
Sbjct  299   GCATGTAAATATGTTGGTGCATTTTGTAGATAATAAAATGCAAATAAGATTCGATTTAAT  358

Query  536   CACCTCCCATAGCCA----TA-TCTGTATCATCTTCTCTCGCCCATGAATGGGTGTCGTGTT  592
             |      |   ||||    || |||| |||  |||     |||    ||   |||| |||
Sbjct  359   GGGATGGTAGAACTATGTATTTTCTAAGAAGTACATTCTTCC--TATTTTTCTATAGT-TT  416

Query  593   ACACGAAAGAGCTCGCCGACAAAAAATTGGCCACCGCACAAGCCAGCACGTGTGAACTCA  652
             | |   |||| |   |    |    ||  || | |    ||| |   ||    |  | |
Sbjct  417   ATATG-TACATCTGGAAGCATAAGATTAATGCAATGTATGTTGGAGTTCATGTTGAGACA  475

Query  653   CGAGACAGCGAAAGATAGCACACGGGAAGTAGAGCCTGCATGCGGAAATAAGGGAATGTT  712
             | |   |||    ||   |   | |  ||    |||| |||| ||  || ||    | |
Sbjct  476   GAGTGCAGGCTGAGGGCAAATTCGTCTTTTTGTG-TGGCATG---AAACAATAGAA---T  528

Query  713   TCACGTAATTTCT-TCGCTTGTTCTACATTTTAG----GTGTTTGAATTTTCAAGATGA-  766
             |||| ||||| || ||| ||| |||  ||  |||    ||| |  ||| |||| |||
Sbjct  529   TGACGGAATTGCTATTTAGGGAGCAAAAGATGAGACTGGTGCCATACATGTCATGAAAAC  588
```

Fig. 2-2

```
Query  767   TTTCTGGA--AACACTTTTGTATCACCAACTAGTACAAGTAAATTGTTATTTTTATGATTT  825
             |||  |  |  ||       ||  |  ||||  ||       |  ||       | ||
Sbjct  589   TTTTTCAATATTACAGGAAGATGGCTAACTTTTATTTCT-CGGTCCTACACAAGGAAATT  647

Query  826   GTTATTTATTTTTGTATCATACCATATCAAATTTTTGTCCATGTCTGACTATAGAAACAA  885
             |  |  |||||||||   |    ||   |    ||       |  ||  |||   | ||
Sbjct  648   TCTCTATATTTTTGTACCGTTCAATTTC--TCTCTTGATTGGTGCATAATTTCTCCAGCTA  706

Query  886   TTAT-AAATTGTTTTTTTATAGAACAATTATAAATTTTGGTAAT---AGAAAATCAGATT  941
             ||||  |||| ||  ||  |||  || ||         |||  |   |  |   |  ||
Sbjct  707   TTATAAAATTTTTGTTTCATTCTTTTATATTTGCTGAGTTTATGTGGGCCCACCTTATG  766

Query  942   TTGTCAGAT-TTGTGATTTTATCTAACGGTTTTTTTGTTCTCAGAACCAAAAATTGCAGA  1000
             |||    ||| ||  ||       | |||| ||||    |  ||  ||  ||  |
Sbjct  767   TTGCAGGATATTGATGTACTCCGTAACTGTCATTTTTGCTTTATGAGAAAGAACT-----  821

Query  1001  TTGTTAAATTGGTTAAATTTAAATTTATTTGACTCTTTGACAAATGAGAAATGTACTTTT  1060
             |||    ||   ||||| | |||||||     |   ||  ||  || |  |||  | ||
Sbjct  822   TTGACTAAAT---ATATA-TAAAAATTATTATTATTTATGGTACAAAATTAATAT-CATTA  877

Query  1061  TTGAATTATGAGAAATGTACTTTTTAAAGATGAAGATAGTAACCTAAAGATGAACTGTGG  1120
               |  |  |  |||  ||  ||| |  ||| ||||  |    ||  | ||| |   ||
Sbjct  878   GACAGAT-CGTTGAATCTA--TTTTTATGATAAATTTATTTA--GAGATATAAATGTTGT  932

Query  1121  GCATACAAGACCACAAGGACGTAGTAAAAAAAAGACCATGGGACGCGTGGATGGTCACAA  1180
             ||      ||       |||||     ||   |  |   |    | | |     ||||
Sbjct  933   ACGTA-TTTTCTACAA--ATCTAGTAAATCTTATGGCACGGAGCAACT-CCTGG-CGAGT  987

Query  1181  AGAAGCATGTTTCATTATTAAGGGTCTGTTTGGATTCTATGCTCTAAACTTGAGTTGTCT  1240
             |||  |   |  ||  ||  |||       |  |  |  ||  |  ||||   ||  ||
Sbjct  988   CTCTGCAT--CTAATTTGCTACCGGTAGAAACCGGAGC--AGACACT-CCCTTGAACTG--CT  1043

Query  1241  AAAGTTGAGGTCTAAAACTTTAGATCACTTTAGCTTTATGTGGTCTGAAGTTTCTATGAG  1300
             |||     |   |||     |  |    ||||  ||     |   |  |||   | ||
Sbjct  1044  ATAATCCTTCATTGGAAGTAGCGCTGCATCTTGCTCAAT--------CCAGATTTCCACGGCG  1098

Query  1301  GTGATCTAAACTTTAGACAACACTTTATATCTCATGTTTAGAGCCTTAATAGTTAAAGTG  1360
             |   |  ||   || |       |||   |   |    ||  ||  |  |  |  |||
Sbjct  1099  TTCTTCAAAGGACTGGATAA---CTCACCTCCCACCGCCATATCTGTATCATCTTGTGTC  1155

Query  1361  GTCTAAAATTTAATGGCTAATAAGCTTTAGTCTATAGGATCTAAACAGTCAGGGTCTAAG  1420
             | |  |  |||||    | ||  ||  |||||| |  |  | ||| |||   |  ||||
Sbjct  1156  G-CCCACA-TGAATGGGT--GTCGTGTTACACGA-AACAGCT-CGCAGACAAAAATTAGG  1209

Query  1421  ACCGCCGGCACACAAGCAGCACTCGTCCTGTGTACTGGACCAAGGGA-CGCGCGAACGGG  1479
             ||  |  ||||||||||| |||| |  |       |||     |   ||| |||||||
Sbjct  1210  CCACCGCACAAGCTAGCACATGTGAACTCACGAGACCGCGAAAGATAGCACACGTACGGG  1269
```

Fig. 2-3

```
Query  1480  CACAGTGGAGTCTTCATTACGCATTGAGGATCCAAAACATACTGCAA--TTCTTACTTTCT  1538
             |||  |||  ||  |||         |  |  ||||       ||  ||  |||| ||  ||  |
Sbjct  1270  ---AAGTAGAGCCTGCATGCGGAAATAAGG------GCATGTTAGTGTAATTTCTTGGCTTTT  1324

Query  1539  AAGGGAGTGAAATATATTTAA--CTTTAATAAAATCTAT--ACAAAAAATTATAAACATTTA  1596
             |  |    |  |    |  |  ||||  |||||  |||||  |  |
Sbjct  1325  TCTATATTTCAGGTTCTTAAATTTTTAAGATGATTTCTGACAACACTTTTGTATCACCAA   1384

Query  1597  -TAGTACCAAATAAATATCATCAGATTGATTATAGAATT---CATAGTAAAATTAATTGGA  1653
             ||| |   ||  ||||       ||||   |  |  ||  ||  ||  |
Sbjct  1385  CTATTATAAGTAAATTGTTACTTTTATGATTTGTTATTTATCATTGTATCATACGATATC  1444

Query  1654  AACATAAATATTGATAATGTTTTCTTATAACTCAAAA----TTTAGAAATGTTTGACTTAT  1710
             || ||  |  ||| ||  ||||  |||| ||||  ||  |  ||  ||  ||| ||
Sbjct  1445  AATTTATCCCTGTCTAA-CTATAGAAATAATTAAAAATTATTAATTATTTTTTGCTAAC  1503

Query  1711  ATAAAA--CCTAGAATTGT-----ATTCCTTA--TGAAACGGAGGAGTATA|TATATATTTAAAG  1765  ③
             |   |||  |  |  |  |  |||  |  |  |  ||  |  ||||| ||||||
Sbjct  1504  ACAAAATCAGATTTTTGTCAGATTTGTGATTTGAAATTTGGCGGA--G|TATATAATTAAAG  1562

Query  1766  TAACCTTTAATG-------CTCTCTGCTACGGTGCTACAGGTCGCCTCTGGTCCTAGAGCTGC  1821
             |||||||||||    ||||||||||||||||||||   |||||   ||||||||    ||
Sbjct  1563  TAACCTTTAATGCTCGCTCTCTGCTACGGTGCTACTGGTCG--TCTGGTCATAGACGAGC  1620

Query  1822  AAATTAAAAGCTGACAATCCAAAAGTTCTCGATTTT-----ATTGAATTGACGTGCCTACC  1877
             |||||||||||||||||| |||  |||| |||  ||||||||||||||
Sbjct  1621  --TGTAAAAGCTGACAATCCAAAGGTTTTGTATTTTATTTATTGAATTGACGTGCCTTTG  1678

Query  1878  AATTAGGTTCACTTGTTGGAACCCGGCCGTGATACACGAGGCATAGAG|CGCATCAGCTCT  1937
             ||||||||||||||||||||||  |||||||||| ||||||||| ||   | |
Sbjct  1679  AATTAGGTTCACTTGTTGGAATCCGGCCGTGATGCACGAGGCATGGAG-GGA--------  1729

Query  1938  CCATCCATCCACCATGCATGGAGTGGTAGCT|GGAGGCGCCTGGCGTTCTATAAATAGAGG  1997  ②
             ||||   |  |  |  | |  | |||    |||  ||| ||||||||||||||||||
Sbjct  1730  CCATGGA-GGGCTAGGCTTTG--GTAGCTGAA|GGCGGCCCCTGGCATTCTATAAATAGAGA  1787

Query  1998  GTTGCTCGCCACCATCCTC|------------|AGCACAAGAACTCCTCGTCCCAAGTCTTCG  2046  ①
             ||| |||||||  |||||   |||||||||||||||||||||||||
Sbjct  1788  GTGGCTCGCCTCCATCCTC|TGCACACACAC|AGCACAAGAACTCCTCGTGCCAAGTCTTCG  1847

Query  2047  TCTTGAGTGC-ACACAGAACAACATTGGCGGCCAGTAGCTAACTTTAGTAGCATCGCTCC  2105
             ||||||||||  ||||||||||||| ||||||||||||||||||||||||||||| |||
Sbjct  1848  TCTTGAGTGCAACACAGAACAACATTGACGGCCAGTAGCTAACTTTAGTAGCATCGTTCC  1907

Query  2106  CCATG  2110
             |||||
Sbjct  1908  CCATG  1912
```

Fig. 3-1

Query Range: 80 - 1229
Sbjct Range: 694 - 1811
1170 bp, INT.Score: 648, OPT.Score: 1970
Identity: 781 / 1170 (66%)
Similarity: 781 / 1170 (66%)
Strand: Plus / Plus

```
Query    80    ATTTCGTCACCCATGGACACCCATCCTGGATTAATGCTAAATGTCCATGCATAATCATCC   139
               ||||  ||  ||  ||  ||    ||   |||||||||    ||    ||| ||
Sbjct   694    ATTTCTCCAGCTAT-TATA-AAATTTTGTTTCATTCTTTTATATTTGCTGAGTTTATG    751

Query   140    AAGACATACTTGTTTCATGTGGTAAGATGTTAATATTCTTTTCTATAAATAAATTTGATT   199
                |   |  |   | |||| | |  | | || ||  ||       |      |||| ||
Sbjct   752    TGGGCCCAC----CTTATGTTGCAGGATATTGATGTACTCCGTAACTGTCATTTTTGCTT   807

Query   200    AAAGTCACTATAATTTGACTAAGGACAAAACGGGATTACTTATATTTTAGGCCAGAGGGA   259
                | |  |     |||||||||   |  |   ||| |||| ||||
Sbjct   808    TATGAGAAAGAACTTTGACTAAATATATATAAAAATTA-TTATTATTTA---------------TG   857

Query   260    GTAC-CGTTTAATTTGTCTCGATTGGTCCATAATTTCTCCAACTATTATAAACTTCTTGT   318
               ||||  ||||| |   || ||  ||  ||   |||  |||  |||||||  |
Sbjct   858    GTACAAAATTAATATCATTAGACAGATCGTTGA--ATCTATTTTATGATAAA------------T   909

Query   319    TTCATTTTATTTATATTTGCTGAGTGTATGTGGGACGCACCTTTTGTTGCAGGATATTGA   378
               ||  ||   ||||  || ||    ||||  |   ||  |  |  |   ||||
Sbjct   910    TTATTTAGAGATATAAATGTTGTACGTATTTTCTA--CAAATCTAG-TAAATCTTATGGC    966

Query   379    TGTAAGGAATTCCAGGCGGCGAGTCTCTGCATCTAATTTGGTACCAGTAGAAACCGGAGC   438   ④
               || || |||         |||||||||||||||||||| ||||| ||||||||||||||
Sbjct   967    ACGGAGCAACTCC---TGGCGAGTCTCTGCATCTAATTTGCTACCGGTAGAAACCGGAGC   1023

Query   439    ATACCCTCCCATGAACTGCTATAATCCTTCATTAGAAGTAGCGCTGCATCTTACTCAATC   498
                | ||||| ||||||||||||||||||||||||| |||||||||||||||||| ||||||
Sbjct  1024    AGACACTCCCTTGAACTGCTATAATCCTTCATTGGAAGTAGCGCTGCATCTTGCTCAATC   1083

Query   499    CAGATTTCCACGGCGTTCTTCGAAGGACTGGATAACTCACCTCCCATAGCCATATCTGTA   558
               |||||||||| |||||||||| |||||||||||||||||||||||| ||||||||||||
Sbjct  1084    CAGATTTCCACGGCGTTCTTCAAAGGACTGGATAACTCACCTCCCACCGCCATATCTGTA   1143

Query   559    TCATCTTCTCTCGCCC--ATGAATGGGTGTCGTGTTACACGAAAGAGCTCGCCGACAAAA   616
               ||||||| | |||||  |||||||||||||||||||||||||| |||||||| |||||
Sbjct  1144    TCATCTTGTGTCGCCCACATGAATGGGTGTCGTGTTACACGAAACAGCTCGCAGACAAAA   1203

Query   617    AATTGGCCACCGCACAAGCCAGCACGTGTGAACTCACGAGACAGCGAAAGATAGCACA--   674
               | | ||||||||||||||| |||||| ||||||||||||| | |||||||||||||||
Sbjct  1204    ATTAGGCCACCGCACAAGCTAGCACATGTGAACTCACGAGACCGCGAAAGATAGCACACG   1263
```

Fig. 3-2

```
Query   675   ---CGGGAAGTAGAGCCTGCATGCGGAAATAAGGGAATGTTTCACGTAATTTCTTCGCTTG   732
              |||||||||||||||||||||||||||||||| ||||||   |||||||||| ||||
Sbjct   1264  TACGGGAAGTAGAGCCTGCATGCGGAAATAAGGGCATGTTTAGTGTAATTTCTTGGCTTT   1323

Query   733   TTCTACATTTTAGGTGTTTGAATTTTCAAGATGATTTCTGGAAACACTTTTGTATCACCA   792
              ||||  ||||| ||| ||  |||||| ||||||||||||| |||||||||||||||||||
Sbjct   1324  TTCTATATTTCAGGTTCTTAAATTTTAAGATGATTTCTGACAACACTTTTGTATCACCA   1383

Query   793   ACTAGTACAAGTAAATTGTTATTTTTATGATTTGTTATTTATTTTTGTATCATACCATAT   852
              ||||  || |||||||||||||| ||||||||||||||||| ||  |||||||||| |||
Sbjct   1384  ACTATTATAAGTAAATTGTTACTTTTATGATTTGTTATTTATCATTGTATCATACGATAT   1443

Query   853   CAAATTTTTGTCCATGTCTGACTATAGAAACAATTATAAATTGTTTTTTTATAGAACAAT   912
              | ||||| |  ||  |||||||||||||||| ||| |||||||           |||||
Sbjct   1444  C-AATTTAT--CCCTGTCTAACTATAGAAATAATTAAAAATT------------ATTAAT   1488

Query   913   TATAAATTTTGGTAATAGAAAATCAGA-TTTTGTCAGATTTGTGATTT----TATCTAACGG   969
              |||  ||||| |||  ||| |||||||  |||||||||||||||||||||   || | |||
Sbjct   1489  TAT--TTTTTGCTAACACAAAATCAGATTTTTGTCAGATTTGTGATTTGAAATTTGGCGG   1547

Query   970   TTTTTTTGTTCTCAGAACCAAAAATTGCAGATTGTTAAATTGGTTAAATTTAAATTTATT   1029
                |||   ||  ||   || ||  ||| ||  ||  |||   ||      |||  ||| |
Sbjct   1548  AGTATATAATTAAAGTAACCTTTAATGCTCGCTCTCTGCTACGGT----GCTACTGGTCGT   1604

Query   1030  TGACTCTTTGAC-AAATGAGAAATGTACTTTTTTGAATTATGAGAAATGTACTTTTTAAA   1088
              || || |||  |     || ||| ||  ||       ||    | ||||| |||| |||
Sbjct   1605  CTGGTCATAGACGAGCTGTAAAAGCTGACAATCCAAAGGTTTGTATTTATTTATTGAA   1664

Query   1089  GATGAAG-ATAGTAACCTAAAGATGAACTGTGGGCATACAAGACCACAAGGACGTAGTAA   1147
              |||       |    |  ||| |||  | |  ||||  ||    ||     |||  | |
Sbjct   1665  -TTGACGTGCCTTTGAATTAGGTTCACTTGTTGGAAT--CCGGCCGTGATGCACG--AGGCA   1721

Query   1148  AAAAAAGACCATGGGACGCGTGG---ATGGT----CACAAAGAAGCATGTTTCATT---ATTAA   1201
              |    ||||||||||    ||   ||   |||   ||| |   ||  |||| || ||
Sbjct   1722  TGGAGGGACCATGGAGGGCTAGGCTTTGGTAGCTGAAGGCGGCCCCTGGCATTCTATAAA   1781

Query   1202  ---GGGTCTGTTTGGATTCTATGCTCTAAAC   1229
                 | ||  | |  || | || ||||   ||
Sbjct   1782  TAGAGAGTGGCTCGCCTCCATCCTCTGCAC   1811
```

```
Query Range: 43 - 1503
Sbjct Range: 456 - 1911
1502 bp, INT.Score: 254, OPT.Score: 678
Identity: 712 / 1502 (47%)
Similarity: 712 / 1502 (47%)
Strand: Plus / Plus Query    43   TTCGACTAGCGGATTCGGCCGCGGTCGTGGCGA-GCCCATTTCGTCACCCATGGACACCC   101
              ||  |||       | | | |||   |    || |||||||  |   || |   |
Sbjct   456   TTGGAGTTCATGTTGAGACAGAGTGCAGGCTGAGGGCAAATTCGT---CTTTTTGTGTGGC  513

Query   102   ATCCTGGATTAATGCTAAATGTCCATGCATAATCATCCAAGACATACTTGTTTCATGTGG   161
              ||    |  |  |   | | ||   |||||| ||  || |   |   | |    | |||
Sbjct   514   ATGAAACAAT-AGAATTGACGGAATTGC-TATTTA-GGGAGCAAAAGATGAGACTGGTGC   570

Query   162   TA-AGATGTTAATATTCTTTTCTATAAATAAATTTGATTAAAGTCACTATAATTTGAC--T   219
              || | |||  ||||  ||||   || ||| |    | || |    |   |||| |   |
Sbjct   571   CATACATGTCATGAAAACTTTTTCAATATTACAGGAAGATGGCTAACTTTTATTTCTCGG   630

Query   220   AAGGACAAAACGGGATTACT--TATATTTTAGGCCAGAGGGAGTACCGTTTAATTTGTCTC   278   ⑤
              |||  ||   |  ||||  ||   ||||||||| ||||| ||||
Sbjct   631   TCCTACACAAGGAAATTTCTCTATATTTT----------------TGTACCGTTCAATTTCTCTC   679

Query   279   --GATTGGTCCATAATTTCTCCAACTATTATAAACTTCTTGTTTCATTTTATTTATATTT   336
                ||||||| |||||||||||||  |||||||||  ||||||||||| | ||| ||||||
Sbjct   680   TTGATTGGTGCATAATTTCTCCAGCTATTATAAAATTTTGTTTCATTCTTTTATATTT   739

Query   337   GCTGAGTGTATGTGGGACGCACCTTTTGTTGCAGGATATTGATGTA---AGGAA-TTCCA   392
              ||||||| ||||||| |||||||||||||||||||||||||||||   ||| |  ||
Sbjct   740   GCTGAGTTTATGTGGG-CCCACCTTATGTTGCAGGATATTGATGTACTCCGTAACTGTCA   798

Query   393   GGCGGCGAGTCTCTGCATCTAATTTG--GTACCAGTAGAAACGGAGCATACCCTCCCATG   451
              |  |  |  | |  ||  |||  |    ||   |||  | |   ||    | || |
Sbjct   799   TTTTTGCTTTATGAGAAAGAACTTTGACTAAATATATATAAAAATTATTATTATTTATGG   858

Query   452   AACTGCTATAATCCTTCATTAGAAGTAGCGCTGCATCT--TACTCAATCCAGATTTCCACG   510
              ||    ||||    |||||||| |  |  ||   ||      |  |  | |  | ||||
Sbjct   859   TACAAAATTAAT--ATCATTAGACAGATCGTTGAATCTATTTTTATGATAAATTTATTTA   916

Query   511   GCGTTCT------TCGAAGGACTGGATAACTCACCTCCCATAGC-CATATC-TGTATCATC   563
              |||| |       |  |||     |||  | |  |   |||  ||| |   ||| ||||
Sbjct   917   GAGATATAAATGTTGTACGTATTTTCTACAAATCTAGTAAATCTTATGGCACGGAGCAAC   976

Query   564   TTCTCTCGCCCATGAATGGGTGTCGTGTTACACG-AAAGAGC-TCGCCGACAAAAAATTG   621
              | ||  ||    |    |  |||  ||  |||   ||||  | |||| |  |   |||
Sbjct   977   TCCTGGCGAGTCTCTGCATCTAATTTGCTACCGGTAGAAACGGAGCAGACACTCCCTTG   1036
```

Fig. 4-2

```
Query   622   GCCACCGCACAAGCCAGCACGTGTGAACTCACGAGACAGCGAAAGATAGCACACGGGAAG   681
              |  | ||| ||  :  |||  || | ||| :           | |||  |
Sbjct   1037  AACTGC-TATAATCCTTCA----TTGGAAGTAGCGCTGCATC----------TTGCTCAATCCAGA   1087

Query   682   TAGAGCCTGCATGC--GGAAATAAGGGAATGTTTCACGTAATTTCTTCGCTTGTTCTACAT   740
              |    |      |   |||  |  |      ||||       |  |    |      |||
Sbjct   1088  TTTCCACGGCGTTCTTCAAAGGACTGGATAACTCACCTCCCACCGCCATATCTGTATCAT   1147

Query   741   TTTAGGTGTTTGAATTTTCAAGATGATTTCTGGAAACAC-TTTTGTATCACCAACTAGTA   799
              ||  ||||       | |   :   |    |   ||||  ||  ||   |    |
Sbjct   1148  CTT--GTGTCGCCCACATGAA-TGGGTGTCGTGTTACACGAAACAGCTCGCAGACAAAAA   1204

Query   800   CAAGTAAATTGTTATTTTTATGATTTGTTATTTATTTTTGTATCATACCATATCAAATTT   859
              ||    |    |      |||  |  ||| ||              |    ||| ||||
Sbjct   1205  TTAGGCCACCGCACAAGCTAGCACATGTGAACTCACGAGACCGCGAAAGATAGCACACGT   1264

Query   860   TTGTCCATGTCTGACTATAGAAACAATTATAAATTGTTTTTTTATAGAACAATTATAAAT   919
              |  |    | || |    |   ::   ||||  | |||| | || |   | | | ||
Sbjct   1265  ACGGGAAGTAGAGCCTGCATGCGGAA---AT--AAGGGCATGTTTAGTGTA-ATTTCTTGGC   1320

Query   920   TTTGGTAATAGAAAATCAGATTTGTCAGATTTGTGATTTTATCTAACGGTTTTTTTGTT   979
              |||  | |  | ||| || ||| |  ||| ||  ||| | |||    |  |||||
Sbjct   1321  TTT--TTCTA-TATTTCAGGTTCTTAAATTTTTAAGATGATTTCTGACAACACTTTTGTA   1377

Query   980   CTCAGAACCAAAAATTGCAGATTGTTAAATTGGTTAAATTTAAATTTATTTGACTCTTTG   1039
                 |   |    |||  |||| |||||| | |  | | |  ||   |||| |  |  |
Sbjct   1378  TCACCAACTATTATAAGTAAATTGTT-ACTTTTATGATTTGTTATTTATCATTGTATCAT   1436

Query   1040  ACAAATGAGAAATGTACTTTTTTGA--ATTATGAGAAAT-GTACTTTTTAAAGATGAAGA   1096
              |||    |||    |  || |||||    ||| || |   ||  | |||   ||  |
Sbjct   1437  ACGATATCAATTTATCCCTGTCTAACTATAGAAATAATTAAAAATTATTAATTATTTTTT   1496

Query   1097  TAGTAACCTAAAGATGAACTGTGGGCATA---CAAGACCACAAGGACGTAGTAAAAAAAAG   1154
              | ||||    |  |   | ||  |        | ||    ||   |  | | | ||| |
Sbjct   1497  TGCTAACACAAAATCAGATTTTTGTCAGATTTGTGATTTGAAATTTGGCGGAGTATATA-   1555

Query   1155  ACCATGGGACGCGTGGATGGTCACAAAGAAGCATGTTTCATTATTAAGGGTCTGTTTGGA   1214
              |   |   |  |  |   ||| ||| |      | | |  |  |    |||| |    |
Sbjct   1556  ATTAAAGTAACCTTTAATGCTCGCTCTCTGCTACGGTGC--TACTGGTCGTCTGGTCATA   1613

Query   1215  TTCTATGCTCTAAACTTGAGTTGTCTAAAGTTGAGGTCTAAAACTTTAGATCACTTTAGC   1274
              |  | | ||||     ||| |   ||||  |  | |  | ||| ||| ||  |  ||
Sbjct   1614  GACGA-GCTGTAAAAGCTGACAATCCAAAGGTTTTGTATTTTA-TTTA-TTGAATTGA-C   1669

Query   1275  TTTATGTGGTCTGAAGTTTCTATGAGGTGATCTAAACTTTA--GACAACAC-TTTATATC   1331
                | | |||       ||| ||    | |  ||| |||     |  | ||  |  | |
Sbjct   1670  GTGCCTTTGAATTAGGTTCACTTGTTGGAATCCGGCCGTGATGCACGAGGCATGGAGGGA   1729
```

Fig. 4-3

```
Query  1332  TCATGTTTAG-----AGCCTTAATAG-TTAAAGTGG---TCTAAAATTTAATGGCTA-ATAAG  1384
             | | |       |    | |  | |  | | | | | | |    | |   | |    | | | |
Sbjct  1730  CCATGGAGGGCTAGGCTTTGGTAGCTGAAGGCGGCCCCTGGCATTCTATAAATAGAGAGT  1789

Query  1385  CTTTAGTCTATAGGATCTAAACAGTCAGGGTCTAAGACCGCCGGCACACAAG-CAGC--AC  1442
             | | ||   |    ||| || | |       |||| | ||       |||| |   | |
Sbjct  1790  GGCTCGCCTCCATCCTCTGCACACACACAGCACAAGAACTCCTCGTGCCAAGTCTTCGTC  1849

Query  1443  TCGTCCTGTGTACTGGACCA-AGGGACGCGCGAACGGGCACAGTGGAGTCTTCATTACGC  1501
             | |          | || | |   ||||  |   ||| |   |   | | | | || | |
Sbjct  1850  TTGAGTGCAACACAGAACAACATTGACGGCCAGTAGCTAACTTTAGTAGCATCGTTCCCC  1909

Query  1502  AT  1503
             ||
Sbjct  1910  AT  1911
```

Fig. 5
(A)
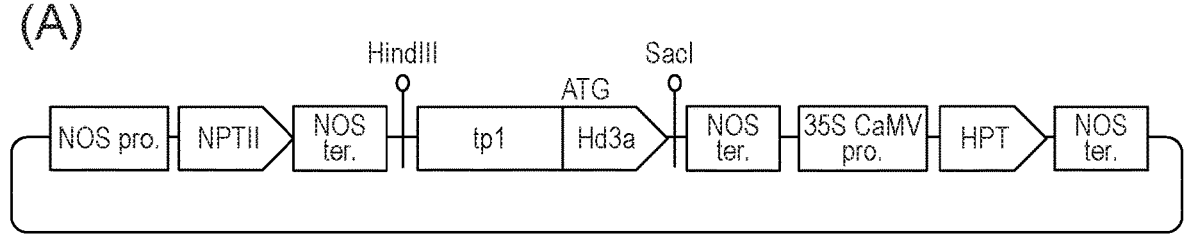
(B)
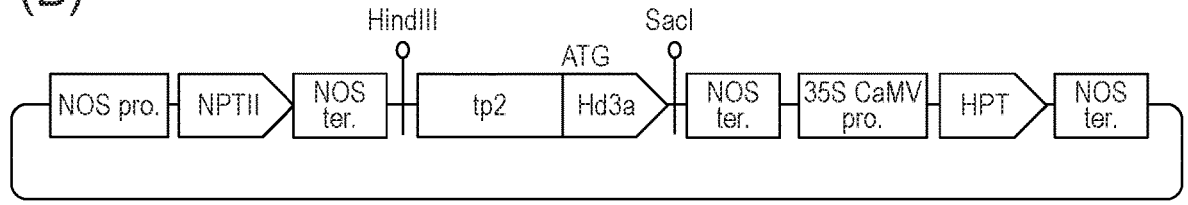

SEQUENCE LISTING

```
<160> NUMBER OF SEQ ID NOS: 15

<210> SEQ ID NO 1
<211> LENGTH: 95
<212> TYPE: DNA
<213> ORGANISM: Saccharum officinarum
<220> FEATURE:
<221> NAME/KEY: misc_feature
<222> LOCATION: (41)..(41)
<223> OTHER INFORMATION: n represents none or A

<400> SEQUENCE: 1
agcacaagaa ctcctcgtsc caagtcttcg tcttgagtgc nacacagaac aacattgrcg      60
gccagtagct aactttagta gcatcgytcc ccatg                                 95

<210> SEQ ID NO 2
<211> LENGTH: 48
<212> TYPE: DNA
<213> ORGANISM: Saccharum officinarum

<400> SEQUENCE: 2
ggmggcscct ggcrttctat aaatagagrg tkgctcgccw ccatcctc                   48

<210> SEQ ID NO 3
<211> LENGTH: 181
<212> TYPE: DNA
<213> ORGANISM: Saccharum officinarum
<220> FEATURE:
<221> NAME/KEY: misc_feature
<222> LOCATION: (26)..(29)
<223> OTHER INFORMATION: gnhs represent none or ctcg
<220> FEATURE:
<221> NAME/KEY: misc_feature
<222> LOCATION: (55)..(56)
<223> OTHER INFORMATION: gnhs represent none or cc
<220> FEATURE:
<221> NAME/KEY: misc_feature
<222> LOCATION: (74)..(75)
```

<223> OTHER INFORMATION: gnhs represent none or aa
<220> FEATURE:
<221> NAME/KEY: misc_feature
<222> LOCATION: (110)..(113)
<223> OTHER INFORMATION: gnhs represent none or attt

<400> SEQUENCE: 3

| | | |
|---|---|---|
| tatatawtta aagtaacctt taatgnnnnc tctctgctac ggtgctacwg gtcgnntctg | 60 |
| gtcmtagass wgcnnwktaa aagctgacaa tccaaargtt ytskattttn nnnattgaat | 120 |
| tgacgtgcct wysaattagg ttcacttgtt ggaayccggc cgtgatrcac gaggcatrga | 180 |
| g | 181 |

<210> SEQ ID NO 4
<211> LENGTH: 505
<212> TYPE: DNA
<213> ORGANISM: Saccharum officinarum
<220> FEATURE:
<221> NAME/KEY: misc_feature
<222> LOCATION: (180)..(181)
<223> OTHER INFORMATION: gnhs represent none or ac
<220> FEATURE:
<221> NAME/KEY: misc_feature
<222> LOCATION: (282)..(285)
<223> OTHER INFORMATION: gnhs represent none or cgta
<220> FEATURE:
<221> NAME/KEY: misc_feature
<222> LOCATION: (465)..(465)
<223> OTHER INFORMATION: n represents a
<220> FEATURE:
<221> NAME/KEY: misc_feature
<222> LOCATION: (473)..(474)
<223> OTHER INFORMATION: gnhs represent none or gt

<400> SEQUENCE: 4

| | | |
|---|---|---|
| ggcgagtctc tgcatctaat ttgstaccrg tagaaaccgg agcakacmct cccwtgaact | 60 |
| gctataatcc ttcattrgaa gtagcgctgc atcttrctca atccagattt ccacggcgtt | 120 |
| cttcraagga ctggataact cacctcccay mgccatatct gtatcatctt ststcgcccn | 180 |
| natgaatggg tgtcgtgtta cacgaaasag ctcgcmgaca aaaawtwggc caccgcacaa | 240 |
| gcyagcacrt gtgaactcac gagacmgcga aagatagcac annnncggga agtagagcct | 300 |
| gcatgcggaa ataagggmat gtttmrygta atttcttsgc ttkttctaya tttyaggtky | 360 |
| ttraatttty aagatgattt ctgrmaacac ttttgtatca ccaactakta yaagtaaatt | 420 |
| gttayttta tgatttgtta tttatywttg tatcatacsa tatcnaattt wtnnccmtgt | 480 |
| ctractatag aaayaattaw aaatt | 505 |

<210> SEQ ID NO 5
<211> LENGTH: 125
<212> TYPE: DNA
<213> ORGANISM: Saccharum officinarum
<220> FEATURE:
<221> NAME/KEY: misc_feature
<222> LOCATION: (20)..(21)
<223> OTHER INFORMATION: gnhs represent none or tt
<220> FEATURE:
<221> NAME/KEY: misc_feature
<222> LOCATION: (96)..(96)
<223> OTHER INFORMATION: n represents a

<400> SEQUENCE: 5

| | | |
|---|---|---|
| gtaccgttya atttstctcn ngattggtsc ataatttctc carctattat aaamttcttg | 60 |
| tttcattytw tttatatttg ctgagtktat gtgggncsca ccttwtgttg caggatattg | 120 |
| atgta | 125 |

<210> SEQ ID NO 6
<211> LENGTH: 2110
<212> TYPE: DNA
<213> ORGANISM: Saccharum officinarum

<400> SEQUENCE: 6

| | | | | | |
|---|---|---|---|---|---|
| gatacacgat | tgcttgatct | gatttggcgc | acaggaaggg | ctttcgacta | gcggattcgg | 60 |
| ccgcggtcgt | ggcgagccca | tttcgtcacc | catggacacc | catcctggat | taatgctaaa | 120 |
| tgtccatgca | taatcatcca | agacatactt | gtttcatgtg | gtaagatgtt | aatattcttt | 180 |
| tctataaata | aatttgatta | aagtcactat | aatttgacta | aggacaaaac | gggattactt | 240 |
| atattttagg | ccagagggag | taccgtttaa | tttgtctcga | ttggtccata | atttctccaa | 300 |
| ctattataaa | cttcttgttt | cattttattt | atatttgctg | agtgtatgtg | ggacgcacct | 360 |
| tttgttgcag | gatattgatg | taaggaattc | caggcggcga | gtctctgcat | ctaatttggt | 420 |
| accagtagaa | accggagcat | accctcccat | gaactgctat | aatccttcat | tagaagtagc | 480 |
| gctgcatctt | actcaatcca | gatttccacg | gcgttcttcg | aaggactgga | taactcacct | 540 |
| cccatagcca | tatctgtatc | atcttctctc | gcccatgaat | gggtgtcgtg | ttacacgaaa | 600 |
| gagctcgccg | acaaaaaatt | ggccaccgca | caagccagca | cgtgtgaact | cacgagacag | 660 |
| cgaaagatag | cacacgggaa | gtagagcctg | catgcgaaa | taagggaatg | tttcacgtaa | 720 |
| tttcttcgct | tgttctacat | tttaggtgtt | tgaattttca | agatgatttc | tggaaacact | 780 |
| tttgtatcac | caactagtac | aagtaaattg | ttatttttat | gatttgttat | ttattttgt | 840 |
| atcataccat | atcaaatttt | tgtccatgtc | tgactataga | aacaattata | aattgttttt | 900 |
| ttatagaaca | attataaatt | tggtaatag | aaaatcagat | tttgtcagat | ttgtgatttt | 960 |
| atctaacggt | ttttttgttc | tcagaaccaa | aaattgcaga | ttgttaaatt | ggttaaattt | 1020 |
| aaatttattt | gactctttga | caaatgagaa | atgtactttt | ttgaattatg | agaaatgtac | 1080 |
| ttttaaaga | tgaagatagt | aacctaaaga | tgaactgtgg | gcatacaaga | ccacaaggac | 1140 |
| gtagtaaaaa | aaagaccatg | ggacgcgtgg | atggtcacaa | agaagcatgt | tcattatta | 1200 |
| agggtctgtt | tggattctat | gctctaaact | tgagttgtct | aaagttgagg | tctaaaactt | 1260 |
| tagatcactt | tagctttatg | tggtctgaag | tttctatgag | gtgatctaaa | ctttagacaa | 1320 |
| cactttatat | ctcatgttta | gagccttaat | agttaaagtg | gtctaaaatt | taatggctaa | 1380 |
| taagctttag | tctataggat | ctaaacagtc | agggtctaag | accgccggca | cacaagcagc | 1440 |
| actcgtcctg | tgtactggac | caagggacgc | gcgaacgggc | acagtggagt | cttcattacg | 1500 |
| cattgaggat | ccaaaacata | ctgcaattct | tactttctaa | gggagtgaaa | tatatttaac | 1560 |
| tttaataaaa | tctatacaaa | aaattataaa | catttatagt | accaaataaa | tatcatcaga | 1620 |
| ttgattatag | aattcatagt | aaaattaatt | ggaaacataa | atattgataa | tgttttctta | 1680 |
| taactcaaaa | tttagaaatg | tttgacttat | ataaaaccta | gaattgtatt | ccttatgaaa | 1740 |
| cggaggagta | tatatatatt | taaagtaacc | tttaatgctc | tctgctacgg | tgctacaggt | 1800 |
| cgcctctggt | cctagagctg | caaattaaaa | gctgacaatc | caaagttct | cgattttatt | 1860 |
| gaattgacgt | gcctaccaat | taggttcact | tgttggaacc | cggccgtgat | acacgaggca | 1920 |
| tagagcgcat | cagctctcca | tccatccacc | atgcatggag | tggtagctgg | aggcgcctgg | 1980 |
| cgttctataa | atagagggtt | gctcgccacc | atcctcagca | caagaactcc | tcgtcccaag | 2040 |
| tcttcgtctt | gagtgcacac | agaacaacat | tggcggccag | tagctaactt | tagtagcatc | 2100 |

|  |  |
|---|---:|
| gctccccatg | 2110 |

<210> SEQ ID NO 7
<211> LENGTH: 1912
<212> TYPE: DNA
<213> ORGANISM: Saccharum officinarum

<400> SEQUENCE: 7

|  |  |
|---|---:|
| gatcaaagtt gttttgcaac ctcgaacatg ctagcccttg ctggcgtgtg acttaattcg | 60 |
| gcatcaatag tatcagatat gtatgtatgc ctttatgttt gtgaatctaa tgtactgtaa | 120 |
| tgtgtgtgaa ctataacgag attctctact acaatatgtg cgaggggcac aaattatgtc | 180 |
| ctaatgtggt attattgggc tgattgtatt tgtgtccacg cccatgcact tgttcatgta | 240 |
| ttgttgaacc tgtagctttt ctcccaatgt cagacggtga tattttattt tcaaaactgc | 300 |
| atgtaaatat gttggtgcat tttgtagata ataaaatgca ataagattc gatttaatgg | 360 |
| gatggtagaa ctatgtattt tctaagaagt acattcttcc tattttttcta tagtttatat | 420 |
| gtacatctgg aagcataaga ttaatgcaat gtatgttgga gttcatgttg agacagagtg | 480 |
| caggctgagg gcaaattcgt cttttttgtgt ggcatgaaac aatagaattg acggaattgc | 540 |
| tatttaggga gcaaaagatg agactggtgc catacatgtc atgaaaactt ttcaatatt | 600 |
| acaggaagat ggctaacttt tatttctcgg tcctacacaa ggaaatttct ctatattttt | 660 |
| gtaccgttca atttctctct tgattggtgc ataatttctc cagctattat aaaattttg | 720 |
| tttcattctt tttatatttg ctgagtttat gtgggcccac cttatgttgc aggatattga | 780 |
| tgtactccgt aactgtcatt tttgctttat gagaaagaac tttgactaaa tatatataaa | 840 |
| aattattatt atttatggta caaaattaat atcattagac agatcgttga atctattttt | 900 |
| atgataaatt tatttagaga tataaatgtt gtacgtattt tctacaaatc tagtaaatct | 960 |
| tatggcacgg agcaactcct ggcgagtctc tgcatctaat ttgctaccgg tagaaaccgg | 1020 |
| agcagacact ccccttgaact gctataatcc ttcattggaa gtagcgctgc atcttgctca | 1080 |
| atccagattt ccacggcgtt cttcaaagga ctggataact cacctcccac cgccatatct | 1140 |
| gtatcatctt gtgtcgccca catgaatggg tgtcgtgtta cacgaaacag ctcgcagaca | 1200 |
| aaaattaggc caccgcacaa gctagcacat gtgaactcac gagaccgcga agatagcac | 1260 |
| acgtacggga agtagagcct gcatgcggaa ataagggcat gtttagtgta atttcttggc | 1320 |
| tttttctata tttcaggttc ttaaattttt aagatgattt ctgacaacac ttttgtatca | 1380 |
| ccaactatta taagtaaatt gttactttta tgatttgtta tttatcattg tatcatacga | 1440 |
| tatcaattta tccctgtcta actatagaaa taattaaaaa ttattaatta ttttttttgct | 1500 |
| aacacaaaat cagatttttg tcagatttgt gatttgaaat ttggcggagt atataattaa | 1560 |
| agtaacctttt aatgctcgct ctctgctacg gtgctactgg tcgtctggtc atagacgagc | 1620 |
| tgtaaaagct gacaatccaa aggttttgta ttttatttat tgaattgacg tgcctttgaa | 1680 |
| ttaggttcac ttgttggaat ccggccgtga tgcacgaggc atggagggac catggagggc | 1740 |
| taggctttgg tagctgaagg cggcccctgg cattctataa atagagagtg gctcgcctcc | 1800 |
| atcctctgca cacacacagc acaagaactc ctcgtgccaa gtcttcgtct tgagtgcaac | 1860 |
| acagaacaac attgacggcc agtagctaac tttagtagca tcgttcccca tg | 1912 |

<210> SEQ ID NO 8
<211> LENGTH: 37
<212> TYPE: DNA
<213> ORGANISM: Artificial

```
<220> FEATURE:
<223> OTHER INFORMATION: Synthetic DNA

<400> SEQUENCE: 8
tgattacgcc aagcttgata cacgattgct tgatctg                              37

<210> SEQ ID NO 9
<211> LENGTH: 35
<212> TYPE: DNA
<213> ORGANISM: Artificial
<220> FEATURE:
<223> OTHER INFORMATION: Synthetic DNA

<400> SEQUENCE: 9
gccacttccg gccatgggga gcgatgctac taaag                                35

<210> SEQ ID NO 10
<211> LENGTH: 37
<212> TYPE: DNA
<213> ORGANISM: Artificial
<220> FEATURE:
<223> OTHER INFORMATION: Synthetic DNA

<400> SEQUENCE: 10
tgattacgcc aagcttgatc aaagttgttt tgcaacc                              37

<210> SEQ ID NO 11
<211> LENGTH: 35
<212> TYPE: DNA
<213> ORGANISM: Artificial
<220> FEATURE:
<223> OTHER INFORMATION: Synthetic DNA

<400> SEQUENCE: 11
gccacttccg gccatgggga acgatgctac taaag                                35

<210> SEQ ID NO 12
<211> LENGTH: 38
<212> TYPE: DNA
<213> ORGANISM: Artificial
<220> FEATURE:
<223> OTHER INFORMATION: Synthetic DNA

<400> SEQUENCE: 12
gtagcatcgc tccccatggc cggaagtggc agggacag                             38

<210> SEQ ID NO 13
<211> LENGTH: 36
<212> TYPE: DNA
<213> ORGANISM: Artificial
<220> FEATURE:
<223> OTHER INFORMATION: Synthetic DNA

<400> SEQUENCE: 13
gttctgacgc cacccgggcg cgtacactgt ctgacg                               36

<210> SEQ ID NO 14
<211> LENGTH: 36
<212> TYPE: DNA
<213> ORGANISM: Artificial
<220> FEATURE:
<223> OTHER INFORMATION: Synthetic DNA

<400> SEQUENCE: 14
gtagcatcgt tccccatggc cggaagtggc agggac                               36
```

```
<210> SEQ ID NO 15
<211> LENGTH: 36
<212> TYPE: DNA
<213> ORGANISM: Artificial
<220> FEATURE:
<223> OTHER INFORMATION: Synthetic DNA

<400> SEQUENCE: 15
gttctgacgc cacccgggcg cgtacactgt ctgacg                              36
```

DRUG-INDUCIBLE PROMOTER AND METHOD OF INDUCTING GENE EXPRESSION USING THE SAME

This application claims priority from Japanese Patent Application Nos. 2015-128038 filed Jun. 25, 2015, the contents of all of which are incorporated herein by reference in their entirety.

TECHNICAL FIELD

The present invention relates to a drug-inducible promoter whose transcription activity is activated in the presence of a given drug, an expression vector comprising such drug-inducible promoter, and a method of inducing gene expression using such drug-inducible promoter.

BACKGROUND ART

Genetic information of an organism is transferred through a procedure referred to as the "central dogma" in which DNA information of a functional gene is transcribed into mRNA and mRNA information is translated, so as to synthesize a functional protein. As a result, biofunctions thereof are developed. In the case of plants, in general, genomic DNA, which is an assembly of genetic information formed via aggregation of the parents' haploids, designates the destiny of the cell, which comprises the genomic DNA and that of a plant derived from such cell.

In order to accurately transfer the information of a functional gene of genomic DNA possessed by a cell and develop biofunctions, it is necessary that an adequate gene be expressed under adequate conditions (e.g., adequate time, site, environmental conditions, and drug exposure) at adequate intensity. It is also necessary that expression of a particular gene be strictly regulated.

The time, the site, and the expression intensity of a functional gene are regulated by gene expression regulatory DNA existing in a 5' upstream region of the functional gene. Genomic DNA of a sugarcane plant, which is a commercial crop, is not decoded. Accordingly, it is not easy to obtain gene expression regulatory DNAs for various functional genes. When a gene was to be introduced into a sugarcane plant in the past, accordingly, expression of the gene to be introduced was regulated with the use of gene expression regulatory DNA derived from another plant (Plant Mol. Biol., February 1992; 18 (4): 675-89, Planta 1998, 206: 20-27).

When a functional gene was expressed in a sugarcane plant with the use of gene expression regulatory DNA derived from another plant, occasionally, the time, the site, the intensity, and other conditions of expression thereof were not strictly regulated. Accordingly, development of gene expression regulatory DNA derived from a sugarcane plant, and, in particular, tissue-specific gene expression regulatory DNA, has been strongly awaited in the art.

For example, JP Patent No. 5472089 discloses gene expression regulatory DNA having activity of promoting photosynthetic-tissue-specific gene expression, and, in particular, mature-leaf-specific gene expression, in a sugarcane plant and a technique for regulating gene expression with the use of such gene expression regulatory DNA. Also, JP 2014-003917 A discloses a technique of promoting sugarcane flowering (ear emergence) by allowing a flowering-inducing gene to express under the control of gene expression regulatory DNA having activity of promoting mature-leaf-specific gene expression in a sugarcane plant. In addition, JP Patent No. 5,655,947 discloses gene expression regulatory DNA having activity of promoting mature-leaf-specific gene expression in a sugarcane plant.

Gene expression regulatory DNAs that activate transcription activity in the presence of a given compound are known. Gene expression regulatory DNAs having such features are referred to as "drug-inducible promoters," and drug-inducible promoters in rice and maize plants have been reported (WO 2014/136793 A1).

SUMMARY OF THE INVENTION

Objects to be Attained by the Invention

Currently, drug-inducible promoters that can be used for sugarcane plants and plants related thereto are not known. Under the circumstances described above, an object of the present invention is to provide a novel drug-inducible promoter that can be used at least for sugarcane plants. It is another object to provide a method of inducing gene expression using such promoter.

Means for Attaining the Objects

The present inventors have conducted concentrated studies in order to attain the above objects. As a result, they succeeded in identifying a gene that would be expressed at a high level in the presence of a given compound in a sugarcane plant, and they discovered that a polynucleotide isolated from a 5' upstream region of such gene would function as a drug-inducible promoter. This has led to the completion of the present invention.

Specifically, the present invention includes the following.
(1) A drug-inducible promoter comprising a polynucleotide comprising a first nucleotide sequence having 90% or higher identity to the nucleotide sequence as shown in SEQ ID NO: 1, a second nucleotide sequence having 90% or higher identity to the nucleotide sequence as shown in SEQ ID NO: 2, a third nucleotide sequence having 90% or higher identity to the nucleotide sequence as shown in SEQ ID NO: 3, a fourth nucleotide sequence having 90% or higher identity to the nucleotide sequence as shown in SEQ ID NO: 4, and a fifth nucleotide sequence having 90% or higher identity to the nucleotide sequence as shown in SEQ ID NO: 5 in such an order from the 3' terminal side toward the 5' terminal side.
(2) The drug-inducible promoter according to (1), which comprises a polynucleotide comprising a nucleotide sequence having 90% or higher identity to the nucleotide sequence as shown in SEQ ID NO: 6 or 7.
(3) The drug-inducible promoter according to (1), which enhances expression of a downstream gene in the presence of a plant defense activator.
(4) The drug-inducible promoter according to (3), wherein the plant defense activator is at least one compound selected from the group consisting of probenazole, acibenzolar-S-methyl, tiadinil, and isotianil.
(5) An expression vector comprising the drug-inducible promoter according to any of (1) to (4) and a coding region linked to a region downstream of the drug-inducible promoter.
(6) A method of inducing gene expression comprising introducing the expression vector according to (5) into a plant cell and bringing a plant defense activator into contact with the plant cell, so as to activate transcription activity of a drug-inducible promoter.

(7) The method of inducing gene expression according to (6), wherein the plant cell is derived from a monocotyledon plant.
(8) The method of inducing gene expression according to (7), wherein the monocotyledon plant is a plant of Gramineae.
(9) The method of inducing gene expression according to (8), wherein the plant of Gramineae belongs to the species *Saccharum* in the family Gramineae.
(10) A transgenic plant transformed with the use of the expression vector according to (5).
(11) The transgenic plant according to (10), which is derived from a monocotyledon plant.
(12) The transgenic plant according to (11), wherein the monocotyledon plant is a plant of Gramineae.
(13) The transgenic plant according to (12), wherein the plant of Gramineae belongs to the species *Saccharum* in the family Gramineae.

Effects of the Invention

The present invention can provide a novel drug-inducible promoter that has activity of promoting gene expression specifically in the presence of a given compound, an expression vector comprising such drug-inducible promoter, a transgenic plant produced via introduction of such expression vector, and a method of inducing gene expression using such drug-inducible promoter.

BRIEF DESCRIPTION OF THE DRAWINGS

FIGS. 2-1 to 2-3 show a characteristic diagram demonstrating the results of comparison of regions exhibiting high degrees of identity between the two types of drug-inducible promoters identified in the examples via alignment analysis ("Query" sequence, nucleotides 196-2110 of SEQ ID NO: 6; "Sbjct" sequence, SEQ ID NO: 7).

FIGS. 3-1 to 3-2 show a characteristic diagram demonstrating the results of comparison of other regions exhibiting high degrees of identity between the two types of drug-inducible promoters identified in the examples via alignment analysis ("Query" sequence, nucleotides 80-1229 of SEQ ID NO: 6; "Sbjct" sequence, nucleotides 694-1811 of SEQ ID NO: 7).

FIGS. 4-1 to 4-3 show a characteristic diagram demonstrating the results of comparison of other regions exhibiting high degrees of identity between the two types of drug-inducible promoters identified in the examples via alignment analysis ("Query" sequence, nucleotides 43-1503 of SEQ ID NO: 6; "Sbjct" sequence, nucleotides 456-1911 of SEQ ID NO: 7).

FIG. 5 schematically shows the structure of expression vectors comprising the two types of drug-inducible promoters identified in the examples.

EMBODIMENTS FOR CARRYING OUT THE INVENTION

Figure 1:
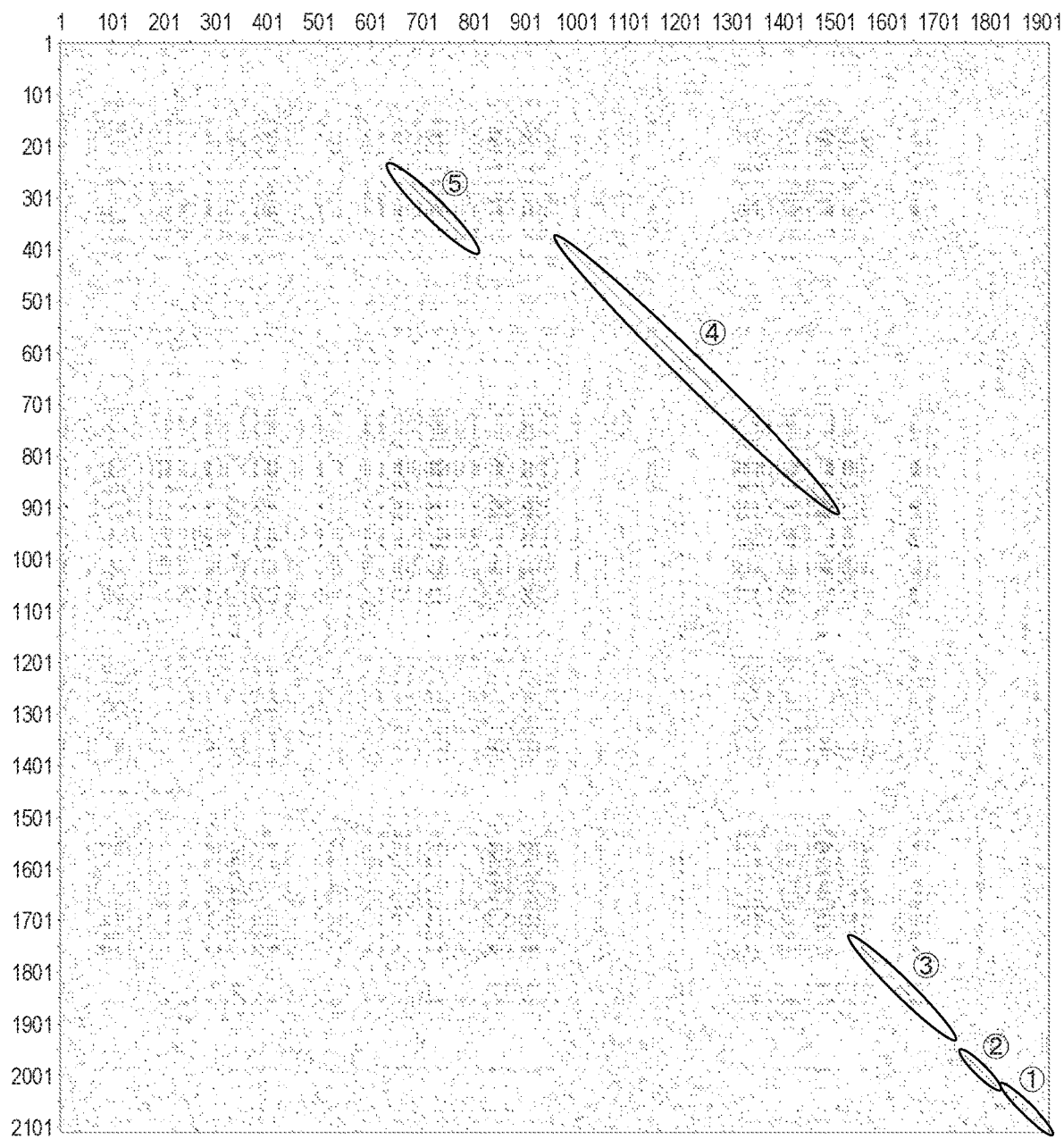
FIG. 1 shows a characteristic diagram demonstrating the results of analysis of the two types of drug-inducible promoters identified in the examples with the use of HarrPlot (GENETYX Corporation).

Hereafter, the present invention is described in detail.
The drug-inducible promoter according to the present invention (hereafter, simply referred to as the "drug-inducible promoter") is capable of activating transcription activity in the presence of a given compound.

A drug-inducible promoter can be defined by the nucleotide sequences as shown in SEQ ID NOs: 1 to 5. The nucleotide sequences as shown in SEQ ID NOs: 1 to 5 are common among a plurality of novel polynucleotides that have been found to be able to activate transcription activity in the presence of a given compound. Specifically, such plurality of polynucleotides each comprise five types of the nucleotide sequences as shown in SEQ ID NOs: 1 to 5 disposed sequentially from the 3' terminal side toward the 5' terminal side. Accordingly, these five types of the nucleotide sequences as shown in SEQ ID NOs: 1 to 5 define regions involved in the drug inducibility of a drug-inducible promoter.

It is highly probable that a polynucleotide comprising a nucleotide sequence having 90% or higher identity to the nucleotide sequence as shown in SEQ ID NO: 1 has functions equivalent to those of the polynucleotide comprising the nucleotide sequence as shown in SEQ ID NO: 1. Similarly, it is highly probable that a polynucleotide comprising a nucleotide sequence exhibiting 90% or higher identity to any of the nucleotide sequences as shown in SEQ ID NOs: 2 to 5 has functions equivalent to those of the polynucleotide comprising any of the nucleotide sequences as shown in SEQ ID NOs: 2 to 5.

Accordingly, a drug-inducible promoter can be defined as comprising a polynucleotide comprising a first nucleotide sequence having 90% or higher identity to the nucleotide sequence as shown in SEQ ID NO: 1, a second nucleotide sequence having 90% or higher identity to the nucleotide sequence as shown in SEQ ID NO: 2, a third nucleotide sequence having 90% or higher identity to the nucleotide sequence as shown in SEQ ID NO: 3, a fourth nucleotide sequence having 90% or higher identity to the nucleotide sequence as shown in SEQ ID NO: 4, and a fifth nucleotide sequence having 90% or higher identity to the nucleotide sequence as shown in SEQ ID NO: 5 in such an order from the 3' terminal side toward the 5' terminal side.

In particular, the first to the fifth nucleotide sequences of the drug-inducible promoter preferably exhibit 95% or higher identity, more preferably 98% or higher identify, and most preferably 99% or higher identity to the nucleotide sequences as shown in SEQ ID NOs: 1 to 5, respectively.

In the drug-inducible promoter, the length of nucleotides between the first nucleotide sequence and the second nucleotide sequence is not particularly limited. For example, it may be 1 to 20 nucleotides, preferably 1 to 15 nucleotides, and more preferably 1 to 11 nucleotides in length. Also, the first nucleotide sequence may be adjacent to the second nucleotide sequence in the drug-inducible promoter.

In the drug-inducible promoter, further, the length of nucleotides between the second nucleotide sequence and the third nucleotide sequence is not particularly limited. For example, it may be 1 to 60 nucleotides, preferably 15 to 55 nucleotides, more preferably 20 to 50 nucleotides, and most preferably 30 to 45 nucleotides in length.

In the drug-inducible promoter, further, the length of nucleotides between the third nucleotide sequence and the fourth nucleotide sequence is not particularly limited. For example, it may be 50 to 1,100 nucleotides, preferably 80 to 1,000 nucleotides, more preferably 100 to 900 nucleotides, and most preferably 110 to 860 nucleotides in length.

In the drug-inducible promoter, further, the length of nucleotides between the fourth nucleotide sequence and the fifth nucleotide sequence is not particularly limited. For example, it may be 1 to 250 nucleotides, preferably 5 to 225 nucleotides, more preferably 5 to 210 nucleotides, and most preferably 10 to 200 nucleotides in length.

Specifically, a drug-inducible promoter comprising the nucleotide sequences as shown in SEQ ID NOs: 1 to 5 in such an order from the 3' terminal side toward the 5' terminal side may be a polynucleotide as shown in SEQ ID NO: 6 or 7. It is highly probable that a polynucleotide comprising a nucleotide sequence having 90% or higher identity to the nucleotide sequence as shown in SEQ ID NO: 6 or 7 has functions equivalent to those of the polynucleotide comprising the nucleotide sequence as shown in SEQ ID NO: 6 or 7. A drug-inducible promoter may be a polynucleotide comprising a nucleotide sequence having 90% or higher identity to the nucleotide sequence as shown in SEQ ID NO: 6 or 7. A drug-inducible promoter is preferably a polynucleotide comprising a nucleotide sequence having 95% or higher identity to the nucleotide sequence as shown in SEQ ID NO: 6 or 7, it is more preferably a polynucleotide comprising a nucleotide sequence having 98% or higher identity to the nucleotide sequence as shown in SEQ ID NO: 6 or 7, and it is most preferably a polynucleotide comprising a nucleotide sequence having 99% or higher identity to the nucleotide sequence as shown in SEQ ID NO: 6 or 7. Nucleotide sequences can be compared in accordance with a conventional technique. For example, the sequence identity as described above can be determined with the use of the Basic Local Alignment Search Tool (BLAST at the National Center for Biological Information, U.S.A.) with the default settings.

A drug-inducible promoter may comprise a polynucleotide comprising a nucleotide sequence derived from the nucleotide sequence as shown in SEQ ID NO: 6 or 7 by deletion, substitution, addition, or insertion of one or more nucleotides. For example, a polynucleotide comprising a nucleotide sequence derived from the nucleotide sequence as shown in SEQ ID NO: 6 or 7 by deletion, substitution, addition, or insertion of 1 to 100 nucleotides, preferably 1 to 50 nucleotides, and more preferably 1 to 10 nucleotides is within the scope of the drug-inducible promoter whose transcription activity is activated in the presence of a given compound.

For example, a drug-inducible promoter may be a polynucleotide comprising a nucleotide sequence derived from the nucleotide sequence as shown in SEQ ID NO: 6 or 7 by deletion of 100, 200, 300, 400, 500, 600, 700, 800, 900, or 1,000 continuous nucleotides from the 5' terminus and/or the 3' terminus. Nucleotides can be deleted in accordance with a technique known to a person skilled in the art, such as PCR or restriction enzyme treatment.

When designing a nucleotide sequence derived from the nucleotide sequence as shown in SEQ ID NO: 6 or 7 by deletion, substitution, addition, or insertion of one or more nucleotides, a promotor analysis tool known to a person skilled in the art (e.g., Bio Informatics and Molecular Analysis Section (http://www-bimas.cit.nih.gov/molbio/proscan/); Prestridge, D. S., 1995, Predicting Pol II Promoter Sequences Using Transcription Factor Binding Sites, J. Mol. Biol., 249: 923-32) may be used, so as to search for a region involved in promoter functions, thereby preventing the loss of functions of a promoter.

In addition, a drug-inducible promoter may be a polynucleotide comprising a nucleotide sequence hybridizing under stringent conditions to DNA comprising a sequence complementary to a full-length or a part of the nucleotide sequence as shown in SEQ ID NO: 6 or 7. Such polynucleotide is also within the scope of the drug-inducible promoter whose transcription activity is activated in the presence of a given compound. Under the "stringent conditions," a so-called specific hybrid is formed, but a non-specific hybrid is not formed. Under such conditions, for example, hybridization is carried out in a solution containing 2-6×SSC (1×SSC composition: 0.15 M NaCl, 0.015 M sodium citrate, pH 7.0) and 0.1% to 0.5% SDS at 42° C. to 55° C., and washing is then carried out in a solution containing 0.1-0.2×SSC and 0.1% to 0.5% SDS at 55° C. to 65° C.

As described above, a polynucleotide comprising a particular nucleotide sequence that is different from the nucleotide sequence as shown in SEQ ID NO: 6 or 7 and functioning as a drug-inducible promoter can be identified in a plant that belongs to, for example, the genus *Saccharum* in the family Gramineae. Examples of plants that belong to the genus *Saccharum* include, but are not particularly limited to, *Saccharum officinarum, Saccharum sinense, Saccharum barberi, Saccharum robustum, Saccharum spontaneum, Saccharum edule,* and *Saccharum* spp. hybrids cv. NiF8, and plants related thereto, such as *Sorghum* and *Erianthus*, with *Saccharum* spp. hybrids cv. NiF8 being preferable.

Whether or not a polynucleotide comprising a particular nucleotide sequence that is different from the nucleotide sequence as shown in SEQ ID NO: 6 or 7 is a drug-inducible promoter can be examined via reporter assays or other means known to a person skilled in the art. Reporter assays can be carried out in the manner described below. That is, vectors comprising various types of reporter genes (e.g., the β-glucuronidase gene (GUS), the luciferase gene (LUC), and the green fluorescent protein gene (GFP)) linked to a region under the control (i.e., downstream) of the nucleotide sequence to be examined in terms of the capacity for inducing gene expression are prepared, the resulting vectors are introduced or transiently introduced into the host genome, and the expression levels of the reporter genes are then assayed in the presence and in the absence of the compound. Such reporter genes are not particularly limited, provided that their expression is detectable. Examples thereof include those generally used in the art, such as the CAT gene, the lacZ gene, the luciferase gene (hereafter referred to as "LUC"), the β-glucuronidase gene (hereafter referred to as "GUS"), and the green fluorescent protein gene (hereafter referred to as "GFP").

The reporter gene expression level can be assayed by a method known to a person skilled in the art in accordance with reporter gene type. When a reporter gene is a CAT gene, for example, acetylation of chloramphenicol caused by the gene product may be detected, so as to assay the reporter gene expression level. Each reporter gene expression level can be assayed in the manner described below. When a reporter gene is an lacZ gene, color development of a pigment compound caused by catalytic activity of the gene expression product is detected. When a reporter gene is an LUC gene, fluorescence emitted by a fluorescent compound caused by catalytic activity of the gene expression product is detected. When a reporter gene is a GFP gene, fluorescence emitted by a GFP protein is detected. When a reporter gene is GUS, for example, promoter activity in a host cell can be evaluated by assaying GUS activity in accordance with (i) the method of histochemical GUS staining (EMBO J. 6, 3901-3907, 1987) and/or (ii) the method of Castle &

Morris involving the use of a fluorescent substrate (Plant Molecular Biology Manual, B5, 1-16, 1994; S. B. Gelvin & R. A. Schilperoort, Kluwer Academic Publishers), assaying protein levels in accordance with the method of Bradford (Anal. Biochem., 72, 248-254, 1976), and calculating GUS activity in terms of protein levels (expressed as nmoles 4-MU/min/mg protein).

When a gene other than one of those described above is to be used as a reporter gene, the transcription level thereof may be assayed via, for example, Northern hybridization, RT-PCR, or DNA array techniques. Alternatively, the expression level of a protein encoded by such gene may be assayed via electrophoresis such as SDA-PAGE, Western blotting, or other means.

Transcription activity of the drug-inducible promoter defined as above is activated in the presence of a given compound. An example of such compound is, but is not particularly limited to, a compound having plant defense activity (i.e., a plant defense activator). Plant defense activators are not particularly limited, and examples thereof include probenazole, acibenzolar-S-methyl, tiadinil, and isotianil. A plant defense activator is particularly preferably probenazole (Oryzemate).

When "transcription activity is activated in the presence of a given compound" herein, the expression level of a downstream gene is significantly higher in the presence of such compound than in the absence of such compound, or such expression level is higher at a statistically significant level (e.g., approximately 2-fold, 3-fold, 4-fold, 5-fold, 6-fold, 7-fold, 8-fold, 9-fold, 10-fold, or higher).

When the nucleotide sequence of the drug-inducible promoter is identified, the drug-inducible promoter can be prepared by chemical synthesis, PCR using genomic DNA as a template, or hybridization using a DNA fragment having such nucleotide sequence as a probe. In addition, site-directed mutagenesis may be applied to the polynucleotide comprising the nucleotide sequence as shown in SEQ ID NO: 6 or 7, so as to synthesize a polynucleotide comprising a nucleotide sequence that is different from the nucleotide sequence as shown in SEQ ID NO: 6 or 7. A mutation can be introduced into the polynucleotide comprising the nucleotide sequence as shown in SEQ ID NO: 6 or 7 by a known technique, such as the Kunkel method or the Gapped duplex method, or a method in accordance therewith. For example, a mutation can be introduced with the use of a mutagenesis kit utilizing site-directed mutagenesis, such as Mutant-K (TAKARA) or Mutant-G (TAKARA), or the LA PCR in vitro Mutagenesis Series Kit (TAKARA).

Subsequently, an expression vector comprising the drug-inducible promoter is described.

The expression vector according to the present invention comprises the drug-inducible promoter described above and a coding region linked to a downstream region of the drug-inducible promoter. Such coding region encodes an amino acid sequence from the initiation codon to the termination codon. In other words, the expression vector according to the present invention comprises a drug-inducible promoter operably linked to a particular gene. When a drug-inducible promoter is "operably linked" to a coding region herein, the coding region is transcribed under the control of the drug-inducible promoter in a host cell into which the expression vector is introduced. A drug-inducible promoter may be directly linked to a coding region, or the promoter and the coding region may be indirectly linked to each other via a spacer having an adequate length and an adequate sequence. In the present invention, vectors that can be used to introduce functional genes into plants via *Agrobacterium*, such as pBI, pBII, pPZP (Hajdukiewicz P, Svab Z, Maliga P.: The small, versatile pPZP family of *Agrobacterium* binary vectors for plant transformation, Plant Mol. Biol., 25: 989-94, 1994), pCAMBIA (http://www.cambia.org/main/r_et_camvec.htm), and pSMA vectors, can be preferably used. Use of pBI and pBII binary vectors or intermediary vectors is particularly preferable, and examples thereof include pBI121, pBI101, pBI101.2, pBI101.3, pBII221, and pIG121 vectors. The binary vector is a shuttle vector that is able to replicate in *Escherichia coli* and *Agrobacterium*. When a plant is infected with *Agrobacterium* carrying a binary vector, DNA in a region sandwiched by border sequences (i.e., the LB sequence and the RB sequence) on the vector can be incorporated into plant nuclear DNA (EMBO Journal, 10 (3), 697-704, 1991). In contrast, a pUC vector is able to directly introduce a gene into a plant, and examples thereof include pUC18, pUC19, and pUC9 vectors. Plant virus vectors, such as cauliflower mosaic virus (CaMV) vectors, bean golden mosaic virus (BGMV) vectors, and tobacco mosaic virus (TMV) vectors, can also be used.

An adequate restriction enzyme recognition sequence may be introduced into the drug-inducible promoter and/or the coding region via substitution, insertion, or addition, so as to facilitate ligation and/or insertion into a vector. At the time of insertion into a vector, at the outset, the DNA fragment comprising the drug-inducible promoter and the coding region is cleaved with adequate restriction enzymes, and the cleaved DNA fragment is inserted into a restriction enzyme recognition site or multi-cloning site of an adequate vector DNA, so as to ligate the DNA fragment to the vector.

A coding region is an endogenous or exogenous gene of a target plant, the expression of which is desired. Examples of such gene include, but are not limited to, a gene involved in photosynthesis, a gene involved in translocation, a gene producing a useful substance (e.g., a medicine, pigment, or aromatic component), a gene involved in sugar metabolism, a pest-resistant gene (e.g., an insect-damage-resistant, anti-fungal, antibacterial, or antiviral gene), a gene involved in resistance against environmental stress (i.e., low-temperature, high-temperature, dehydration, photodamage, or ultraviolet radiation stress), and a gene regulating (promoting/suppressing) plant growth.

According to need, an enhancer, an intron, a poly-A addition signal, a 5'-UTR sequence, a selection marker gene, or the like can be linked to the expression vector according to the present invention at an upstream region, the inside, or a downstream region of gene expression regulatory DNA and/or a functional gene.

An enhancer is used to improve, for example, the efficiency of functional gene expression, and an example thereof is an enhancer region comprising an upstream sequence in the CaMV 35S promoter.

Any sequence may be used as a terminator, provided that it is able to terminate transcription of the gene transcribed by the promoter. Examples thereof include a nopaline synthase gene terminator, an octopine synthase gene terminator, and a CaMV 35S RNA gene terminator.

Examples of selection marker genes include the hygromycin-tolerant gene, the kanamycin-tolerant gene, the Bialaphos-tolerant gene, the blasticidin S-tolerant gene, and the acetolactate synthase gene. A selection marker gene may be linked together with a functional gene to the same plasmid, so as to prepare a recombinant vector. Alternatively, a recombinant vector may be prepared by ligating a selection marker gene to a plasmid, and another recombinant vector may be separately prepared by ligating a functional gene to a plasmid. When separately prepared, recombinant vectors are co-transfected into a host.

With the use of recombinant vectors thus prepared, a transformant can be prepared.

A transgenic plant can be prepared by adequately selecting various techniques that have already been established and reported. Preferable examples thereof include the *Agrobacterium* method, the PEG-calcium phosphate method, electroporation, the liposome method, the particle gun method, and microinjection. When the *Agrobacterium* method is employed, protoplasts may be used, tissue sections may be used, or plant bodies may be used (the in planta method). When protoplasts are used, protoplasts are cultured in the presence of *Agrobacterium* carrying Ti plasmids, or protoplasts are fused to *Agrobacterium* spheroplasts (the spheroplast method). When tissue sections are used, aseptically cultured leaf discs or calluses of a target plant may be infected therewith. When the in planta method involving the use of seeds or plant bodies is employed, water-absorptive seeds, seedlings, or potted plants may be directly treated with *Agrobacterium* in a system that does not involve tissue culture supplemented with plant hormones.

Whether or not the gene of interest has been incorporated into a plant body can be inspected via, for example, PCR, Southern hybridization, Northern hybridization, or Western blotting. For example, DNA is prepared from a transgenic plant, DNA-specific primers are designed, and PCR is carried out. Thereafter, the amplified product is subjected to agarose gel electrophoresis, polyacrylamide gel electrophoresis, or capillary electrophoresis, the product is stained with ethidium bromide, an SYBR Green solution, or the like, and the amplified product is detected as a single band. Thus, transformation can be confirmed. Alternatively, PCR may be carried out with the use of primers that have been labeled with a fluorescent dye or the like in advance, and the amplified product may then be detected. In addition, the amplified product may be bound to a solid phase, such as a microplate, and the amplified product may be inspected via fluorescence or enzyme reactions.

Plants that are subjected to transformation in the present invention are not particularly limited. Examples thereof include, but are not particularly limited to, plants of Gramineae, Solanaceae, Brassicaceae, Leguminosae, Rosaceae, Compositae, Liliaceae, Umbelliferae, Caryophyllaceae, Cucurbitaceae, Convolvulaceae, and Chenopodiaceae. Preferable examples include plants of Gramineae, such as *Saccharum, Oryza sativa*, barley, wheat, maize, *Zoysia, Sorghum, Setaria italica*, Japanese millet, *Pennisetum purpureum*, and switchgrass. Use of plants of the species *Saccharum* in the family Gramineae is particularly preferable.

Plant materials that are subjected to transformation in the present invention are, for example, plant tissues, such as roots, stems, leaves, seeds, germs, ovules, ovaries, shoot apices (the growth points at the tips of plant buds), anthers, and pollens, sections of plant tissues, undifferentiated calluses, and cultured plant cells or protoplasts from which cell walls have been removed via enzymatic treatment. When the in-planta method is employed, water-absorptive seeds or entire plant bodies can be used.

In the present invention, the term "transgenic plant" refers to the entire plant body, a plant organ (e.g., root, stem, leaf, petal, seed, or fruit), a plant tissue (e.g., epidermis, phloem, parenchyma, xylem, or fibrovascular bundle), or cultured plant cells.

When cultured plant cells are the targets, a transgenic plant may be reproduced from the resulting transformed cells by reproducing an organ or individual via a known tissue culture technique. A person skilled in the art would readily perform such procedure in accordance with a method that is generally known as a method of reproducing a plant from a plant cell. For example, a plant can be reproduced from a plant cell in the manner described below.

When plant tissues or protoplasts are used as plant materials to be subjected to transformation, plant tissues or protoplasts are cultured in a callus formation medium sterilized with the addition of inorganic elements, vitamins, carbon sources, sugars as energy sources, plant growth regulators (e.g., plant hormones, such as auxin and cytokinin), or the like, so as to form dedifferentiated calluses that amorphously proliferate (hereafter, this procedure is referred to as "callus induction"). The calluses thus formed are transferred to a fresh medium containing a plant growth regulator, such as auxin, so as to achieve further proliferation (passage culture).

It is preferable that callus induction be carried out in a solid medium such as an agar medium and that passage culture be carried out in a liquid medium. Thus, both procedures can be carried out efficiently and with large quantities. Calluses that had proliferated through the passage culture are then cultured under adequate conditions, so as to induce redifferentiation of organs (hereafter, this procedure is referred to as "redifferentiation induction"), and a complete plant body is reproduced at the end. Redifferentiation induction can be carried out by adequately determining types and amounts of various components, such as plant growth regulators, such as auxin and cytokine, and carbon sources, light, temperature, and other conditions of the medium. Via such redifferentiation induction, adventive embryos, adventive roots, adventive buds, adventive stems and leaves, and the like are formed and further grown into complete plants. Alternatively, they may be stored in the state before they grow into complete plants (e.g., encapsulated artificial seeds, dehydrate embryos, or lyophilized cells or tissues).

In addition to the "T1 generation" plants that have been subjected to transformation, progeny plants, such as the "T2 generation" plants that are obtained from seeds of the T1 generation plants and the next generation plants obtained by self-pollination of flowers of the "T2 generation" plants that are found to be transgenic plants via drug selection or Southern analysis are within the scope of the "transgenic plants" of the present invention.

EXAMPLES

Hereafter, the present invention is described in greater detail with reference to the examples, although the technical scope of the present invention is not limited to these examples.

Example 1

In Example 1, at the outset, a sugarcane variety Q165 was subjected to drug treatment with probenazole (8% Oryzemate granules, Meiji Seika Pharma Co., Ltd., 20 g/4 liters of soil) approximately 60 days after it had been planted. The leaves that had expanded from the top were sampled before and after the treatment, and total RNA was extracted using the RNeasy Plant Mini Kit (QIAGEN).

Subsequently, the obtained total RNA was subjected to RNAseq expression analysis (Illumina HiSeq Sequencing, both-ends analysis), so as to obtain read data set. With the use of the assembler (Velvet version 1.2.08), the read data were reassembled into contig sequence information. The contig sequence information resulting from such reassembly was compared with each RNA sequence, and mapping data were obtained using a mapping program (Bowtie version 1.0.0). The resulting data were designated as the original data for RNAseq analysis.

The expression levels of the EST sequences of the original data of the drug treatment group and the non-treatment group were compared, so as to search for EST sequences exhibiting a 100-fold or more increase in expression levels. As a result, a gene that would be strongly induced to express upon administration of probenazole was selected. On the basis of the EST sequence, two types of gene expression regulatory DNAs located in the 5' upstream region of the selected gene were obtained by the Straight Walk method developed by BEX Co., Ltd. Such gene expression regulatory DNAs are drug-inducible promoters whose transcription activity is activated in the presence of a drug, such as probenazole. The two types of drug-inducible promoters mentioned above were designated as tp1 and tp2, respectively, and the nucleotide sequences thereof are shown in SEQ ID NOs: 6 and 7, respectively.

In Example 1, these two types of drug-inducible promoters, tp1 and tp2, were analyzed in terms of nucleotide sequence similarity using HarrPlot included in Genetyx (GENETYX Corporation). The results are shown in FIG. 1. In FIG. 1, the results of analysis for the tp1 nucleotide sequence are shown on the vertical axis, and the results for the tp2 nucleotide sequence are shown on the horizontal axis. By indicating dots in regions where sequences are identical to each other between these nucleotide sequences, a line is shown when sequences are consistent with each other over a particular length. As shown in FIG. 1, five regions exhibiting very high sequence identity were detected in the two types of drug-inducible promoters, tp1 and tp2. The nucleotide sequences of the five regions that are the same for tp1 and tp2 and can be derived from the tp1 and tp2 nucleotide sequences are shown in SEQ ID NOs: 1 to 5.

The nucleotide sequence as shown in SEQ ID NO: 1 is equivalent to a region of nucleotides 2017 to 2110 in the nucleotide sequence as shown in SEQ ID NO: 6, and it is equivalent to a region of nucleotides 1818 to 1912 in the nucleotide sequence as shown in SEQ ID NO: 7. The nucleotide sequence as shown in SEQ ID NO: 2 is equivalent to a region of nucleotides 1969 to 2016 in the nucleotide sequence as shown in SEQ ID NO: 6, and it is equivalent to a region of nucleotides 1759 to 1806 in the nucleotide sequence as shown in SEQ ID NO: 7. The nucleotide sequence as shown in SEQ ID NO: 3 is equivalent to a region of nucleotides 1753 to 1925 in the nucleotide sequence as shown in SEQ ID NO: 6, and it is equivalent to a region of nucleotides 1550 to 1726 in the nucleotide sequence as shown in SEQ ID NO: 7. The results of alignment analysis for tp1 and tp2 comprising the nucleotide sequences as shown in SEQ ID NOs: 1 to 3 are shown in FIGS. 2-1 to 2-3.

The nucleotide sequence as shown in SEQ ID NO: 4 is equivalent to a region of nucleotides 396 to 894 in the nucleotide sequence as shown in SEQ ID NO: 6, and it is equivalent to a region of nucleotides 981 to 1482 in the nucleotide sequence as shown in SEQ ID NO: 7. The results of alignment analysis for tp1 and tp2 comprising the nucleotide sequence as shown in SEQ ID NO: 4 are shown in FIGS. 3-1 and 3-2.

Further, the nucleotide sequence as shown in SEQ ID NO: 5 is equivalent to a region of nucleotides 260 to 382 in the nucleotide sequence as shown in SEQ ID NO: 6, and it is equivalent to a region of nucleotides 661 to 784 in the nucleotide sequence as shown in SEQ ID NO: 7. The results of alignment analysis for tp1 and tp2 comprising the nucleotide sequence as shown in SEQ ID NO: 4 are shown in FIGS. 4-1 to 4-3.

As is apparent from the results of analysis shown in FIG. 1 and the results of alignment analysis shown in FIGS. 2-1 to 4-3, the nucleotide sequences as shown in SEQ ID NOs: 1 to 5 are very similar in tp1 and tp2, and these nucleotide sequences constitute regions that are deeply involved with drug responsiveness of the drug-inducible promoters, tp1 and tp2, identified in Example 1.

Example 2

In Example 2, transcription promoting activity of the two types of drug-inducible promoters, tp1 and tp2, isolated in Example 1 was examined in the presence and in the absence of probenazole. In Example 2, as shown in FIG. 5, a tp1-carrying expression vector (FIG. 5(A)) and a tp2-carrying expression vector (FIG. 5(B)) were constructed.

These expression vectors were constructed with the use of the gene expression vector disclosed in JP 2014-003917 A. The gene expression vector mentioned above was constructed by ligating the expression regulatory region of the ecc0002 gene disclosed in JP 2014-003917 A to cDNA encoding rice Hd3a and ligating the resultant to a plant transformation vector (pIG121-Hm). In Example 2, such gene expression vector is referred to as "ecc0002-Hd3a-pIG121-Hm."

Figure 6:
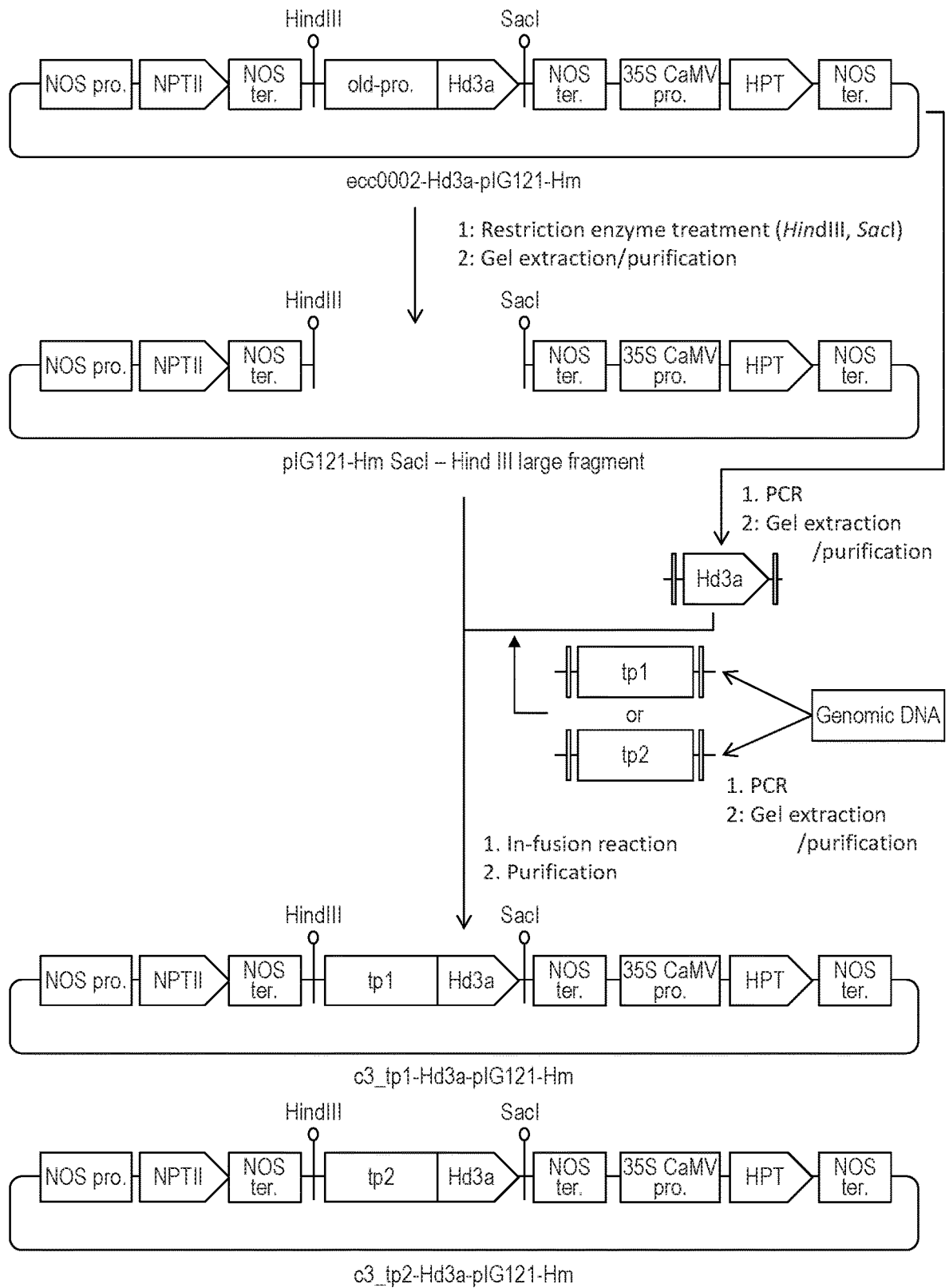
FIG. 6 schematically shows a process for preparing the expression vectors shown in FIG. 5.

More specifically, as shown in FIG. 6, the expression regulatory region of the ecc0002 gene and cDNA encoding rice Hd3a were first removed from ecc0002-Hd3a-pIG121-Hm via restriction enzyme treatment using HindIII and SacI, so as to obtain a pIG121-Hm SacI-Hind III large fragment.

Separately, drug-inducible promoters, tp1 and tp2, were obtained via PCR using the sugarcane variety Q165 genome as a template. The drug-inducible promoter tp1 was amplified via PCR using the forward primer: tgattacgccaagcttGATACACGATTGCTTGATCTG (SEQ ID NO: 8) and the reverse primer: gccacttccggccatGGGGAGCGATGCTACTAAAG (SEQ ID NO: 9). The drug-inducible promoter tp2 was amplified via PCR using the forward primer: tgattacgccaagcttGATCAAAGTTGTTTTGCAACC (SEQ ID NO: 10) and the reverse primer: gccacttccggccatGGGGAACGATGCTACTAAAG (SEQ ID NO: 11).

cDNA encoding rice Hd3a to be linked to the drug-inducible promoter tp1 was amplified via PCR using the forward primer: TAGCATCGCTCCCCatggccggaagtggcagggacag (SEQ ID NO: 12) and the reverse primer: gttctgacgccacccgggcgcgtacactgtctgacg (SEQ ID NO: 13). cDNA encoding rice Hd3a to be linked to the drug-inducible promoter tp2 was amplified via PCR using the forward primer: GTAGCATCGTTCCCCatggccggaagtggcagggac (SEQ ID NO: 14) and the reverse primer: gttctgacgccacccgggcgcgtacactgtctgacg (SEQ ID NO: 15).

Subsequently, the drug-inducible promoter tp1 and cDNA encoding rice Hd3a obtained via PCR were used as templates to ligate the drug-inducible promoter tp1 to cDNA encoding rice Hd3a via PCR. Also, the drug-inducible promoter tp2 and cDNA encoding rice Hd3a obtained via PCR were used as templates to ligate the drug-inducible promoter tp2 to cDNA encoding rice Hd3a via PCR Subsequently, the resulting DNA fragments were each linked to the pIG121-Hm SacI-Hind III large fragment, so as to construct the expression vectors shown in FIG. 5(A) and FIG. 5(B).

With the use of the tp1-carrying expression vector and the tp2-carrying expression vector constructed in the manner described above, Recombinants 1 to 8 were prepared. Recombinants 1 to 7 were prepared with the use of the tp1-carrying expression vector, and Recombinant 8 was prepared with the use of the tp2-carrying expression vector.

Specifically, the prepared expression vectors were electroporated into *Agrobacterium* EHA105 and cultured in LB agar medium containing hygromycin (50 mg/L). The resulting single colony was cultured in LB liquid medium containing hygromycin (50 mg/L), and the resultant was suspended in an 80% glycerol solution. The resulting suspension was designated as a stock solution.

Subsequently, the stock solution was cultured in LB liquid medium containing hygromycin (50 mg/L) overnight, and the recovered cells were suspended in N6 liquid medium. Acetosyringone was added thereto at 20 mg/L, and the resultant was diluted with N6 liquid medium. Thus, the cell solution for infection was prepared.

Subsequently, the calluses of the sugarcane variety Q165 were soaked in the cell solution for infection, so as to infect the calluses with *Agrobacterium* EHA105. After the calluses were soaked therein for approximately 10 minutes, the cell solution for infection was thoroughly suction-removed therefrom, the calluses were seeded in a coculture medium, and culture was conducted at 25° C. in the dark for 4 days. Thereafter, the calluses were seeded in a hygromycin-containing selection medium, culture was conducted at 27° C. in the dark, and drug-resistant calluses were then identified. The calluses that were yellow in color and hard to a certain extent were divided into 4-mm sections, these sections were transferred to a redifferentiation medium, and individuals exhibiting shoots that had grown to 2 to 3 cm or longer were then transferred to a rooting medium.

Figure 7:
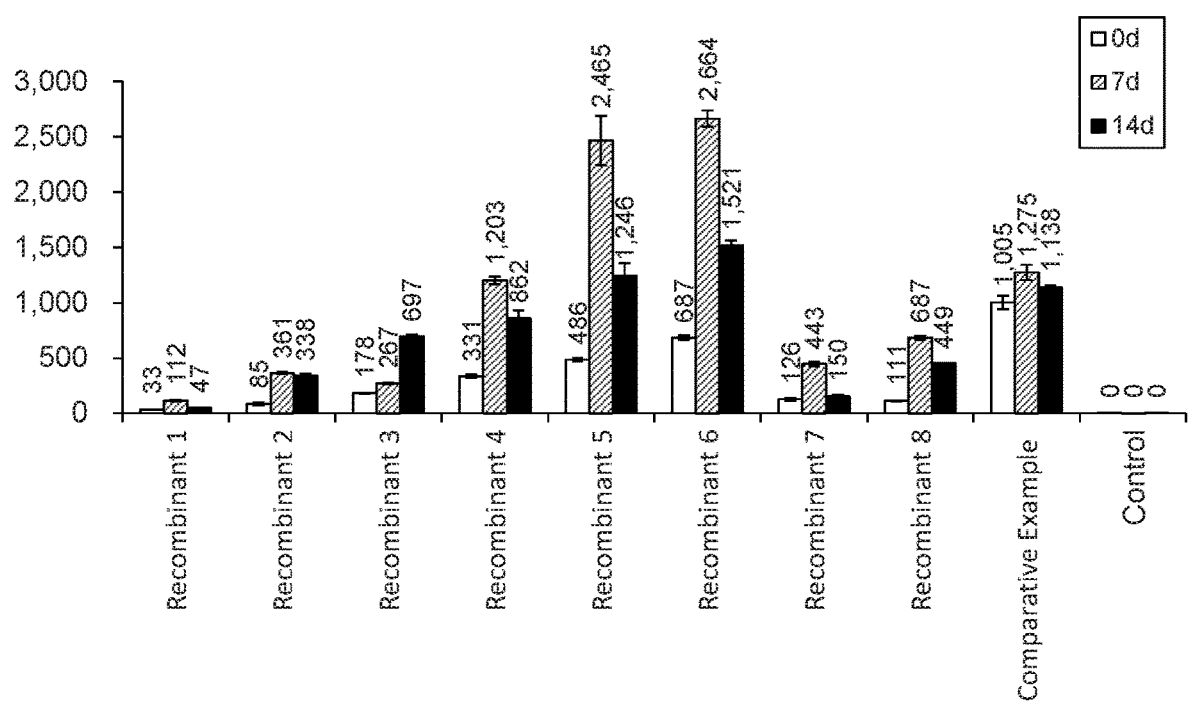
FIG. 7 shows a characteristic diagram demonstrating the results of comparison of gene expression levels in the recombinants prepared in the examples in the presence and in the absence of probenazole.

Recombinants 1 to 8 prepared in the manner described above were treated with Oryzemate granules (8% probenazole, Meiji Seika Pharma Co., Ltd., 20 g/4 liters of soil), and leaves were sampled therefrom 0 days after drug treatment (i.e., immediately before the treatment), 7 days after drug treatment, and 14 days after drug treatment. The RNA levels of the recombinants were quantified using the AB17500 real-time PCR apparatus (Applied BioSystems) in accordance with the SYBR Green method. The results are shown in FIG. 7. A comparative example shown in FIG. 7 concerns a recombinant prepared with the use of ecc0002-Hd3a-pIG121-Hm. The control example shown in FIG. 7 concerns the Q165 wild-type sugarcane variety.

As shown in FIG. 7, the degree of gene expression induction was found to be 3 times as high or higher in the group subjected to probenazole treatment. The results indicate that transcription activity of the two types of drug-inducible promoters, tp1 and tp2, identified and isolated in Example 1 is activated to a significant extent in the presence of probenazole.

The invention claimed is:

1. An expression vector comprising a drug-inducible promoter and a nucleotide coding region operably linked to the drug-inducible promoter,
   wherein the drug-inducible promoter comprises the nucleotide sequence of SEQ ID NO: 6 or 7.

2. A method of inducing gene expression comprising introducing the expression vector according to claim 1 into a plant cell and bringing a plant defense activator into contact with the plant cell, so as to activate transcription activity of the drug-inducible promoter,
   wherein the plant defense activator is probenazole.

3. The method of inducing gene expression according to claim 2, wherein the plant cell is derived from a monocotyledon plant.

4. The method of inducing gene expression according to claim 3, wherein the monocotyledon plant is a plant of Gramineae.

5. The method of inducing gene expression according to claim 4, wherein the plant of Gramineae belongs to the species *Saccharum* in the family Gramineae.

6. A transgenic plant transformed with the expression vector according to claim 1.

7. The transgenic plant according to claim 6, which is derived from a monocotyledon plant.

8. The transgenic plant according to claim 7, wherein the monocotyledon plant is a plant of Gramineae.

9. The transgenic plant according to claim 8, wherein the plant of Gramineae belongs to the species *Saccharum* in the family Gramineae.

* * * * *